US008759043B2

(12) United States Patent
Breuer et al.

(10) Patent No.: US 8,759,043 B2
(45) Date of Patent: Jun. 24, 2014

(54) BIOCATALYTIC PRODUCTION OF AMBROXAN

(75) Inventors: Michael Breuer, Darmstadt (DE); Andrea Hörster, Ludwigshafen (DE); Bernhard Hauer, Fussgönheim (DE)

(73) Assignee: BASF SE, Ludwigshafen (DE)

( * ) Notice: Subject to any disclaimer, the term of this patent is extended or adjusted under 35 U.S.C. 154(b) by 3 days.

(21) Appl. No.: 13/375,996

(22) PCT Filed: Jun. 2, 2010

(86) PCT No.: PCT/EP2010/057696
§ 371 (c)(1),
(2), (4) Date: Dec. 2, 2011

(87) PCT Pub. No.: WO2010/139719
PCT Pub. Date: Dec. 9, 2010

(65) Prior Publication Data
US 2012/0135477 A1     May 31, 2012

(30) Foreign Application Priority Data

Jun. 5, 2009 (EP) .................................... 09162104

(51) Int. Cl.
C12P 17/04 (2006.01)
C12N 1/15 (2006.01)
C12N 1/19 (2006.01)
C12N 1/21 (2006.01)

(52) U.S. Cl.
USPC ................. 435/126; 435/320.1; 435/252.325; 435/254.2; 435/252.33

(58) Field of Classification Search
CPC ............ C12P 17/04; C12N 9/90; C12N 15/70
USPC ............ 435/126, 252.3, 320.1, 254.2, 252.33
See application file for complete search history.

(56) References Cited

FOREIGN PATENT DOCUMENTS

JP     2009060799     *     3/2009
JP     2009060799  A       3/2009

OTHER PUBLICATIONS

Devos et al., Proteins: Structure, Function and Genetics, 2000, vol. 41: 98-107.*
Whisstock et al., Quarterly Reviews of Biophysics 2003, vol. 36 (3): 307-340.*
Witkowski et al., Biochemistry 38:11643-11650, 1999.*
Kisselev L., .Structure, 2002, vol. 10: 8-9.*
International Preliminary Report on Patentability for PCT/EP2010/057696, mailed Dec. 29, 2011.
International Search Report for PCT/EP2010/057696, mailed Jan. 12, 2010.
Database UniProt [Online], Nov. 14, 2006, "Putative two-component system sensor kinase (Frankia alni)," XP002607439, Database accession No. Q05HK2.
Database UniProt [Online], Feb. 1, 2005, "Squalene-hopene cyclase (Zymomonas mobilis)," XP002607434, Database accession No. Q5NM88.
Database UniProt [Online], Nov. 1, 1999, "Putative squalene-hopene cyclase (Streptomyces coelicolor)," XO002607441, Database accession No. Q9X7V9.
Database UniProt [Online], Jun. 12, 2007, "Squalene-hopene cyclase (Bradyrhizobium sp.)," XP002607435, Database accession No. A5EBP6.
Database UniProt [Online], Oct. 13, 2006, "Squalene-hopene cyclase (Rhodopseudomonas palustris)," XP002607440, Database accession No. Q07I43.
Database UniProt [Online], Nov. 14, 2006, "Putative two-component system sensor kinase (Frankia alni)," XP002607439, Database accession No. Z05HK2.
Database UniProt [Online], Oct. 17, 2006, "Squalene-hopene cyclase (Burkholderia ambifaria)," XP002607436, Database accession No. Q0B5S3.
Database UniProt [Online], Oct. 17, 2006, "Squalene-hopene synthase (Burkholderia ambifaria)," XP002607437, Database accession No. Q0B2H5.
Database UniProt [Online], Sep. 2, 2008, "Putative squalene-hopene cyclase (Bacillus anthracis)," XP002607438, Database accession No. B3IZ59.
Neumann, S., et al., "Purification, Partial Characterization and Substrate Specificity of a Squalene Cyclase from Bacillus acidocaldarius," Biol. Chem. Hoppe-Seyler (Aug. 1986), vol. 367, pp. 723-729.
Ochs, D., et al., "Cloning, Expression, and Sequencing of Squalene-Hopene Cyclase, a Key Enzyme in Triterpenoid Metabolism," Journal of Bacteriology (Jan. 1992), vol. 174, No. 1, pp. 298-302.
Ogura, K., et al., "A Novel Substrate for Prenyl Transferase. Formation of a Nonallylic cis-Homofarnesyl Pyrophosphate," Journal of the American Chemical Society (1974), vol. 96, No. 12, pp. 4037-4038.
Perzl, M., et al., "Squalene-hopene cyclase from Bradyrhizobium japonicum: cloning, expression, sequence analysis and comparison to other triterpenoid cyclases," Microbiology (1997), vol. 143, pp. 1235-1242.
Reipen, I.G., et al., "Zymomonas mobilis squalene-hopene cyclase gene (shc): cloning, DNA sequence analysis, and expression in Escherichia coli," Microbiology (1995), vol. 141, pp. 155-161.
Sato, T., et al., "Overexpression of Squalene-Hopene Cyclase by the pET Vector in Escherichia coli and First Identification of Tryptophan and Aspartic Acid Residues inside the QW Motif as Active Sites," Biosci. Biotechnol. Biochem. (1998), vol. 62, No. 2, pp. 407-411.
Snowden, R.L., et al., "Internal Nucleophilic Termination in Biomimetic Acid Mediated Polyene Cyclizations: Stereochemical and Mechanistic Implications. Synthesis of (±)-Ambrox and Its Diastereoisomers," J. Org. Chem. (1992), vol. 57, pp. 955-960.
Tippelt, A., et al., "Squalene-hopene cyclase from Methylococcus capsulatus (Bath): a bacterium producing hopanoids and steroids," Biochimica et Biophysica Acta (1998), vol. 1391, pp. 223-232.
NCBI Database, Nov. 3, 2011, "Squalene-hopene cyclase (Streptomyces coelicolor A3 (2)", Accession No. NP_630836.
NCBI Database, Oct. 23, 2008, "Putative squalene-hopene cyclase (Streptomyces coelicolor A3 (2)", Accession No. CAB39697.1.

* cited by examiner

Primary Examiner — Tekchand Saidha
Assistant Examiner — Md. Younus Meah
(74) Attorney, Agent, or Firm — Drinker Biddle & Reath LLP

(57) ABSTRACT

The invention relates to a process for the biocatalytic production of ambroxan by means of a polypeptide with the activity of a homofarnesol-ambroxan cyclase, which are a novel class of enzymes.

16 Claims, No Drawings

SEQUENCE LISTING

<160> NUMBER OF SEQ ID NOS: 11

<210> SEQ ID NO 1
<211> LENGTH: 6525
<212> TYPE: DNA
<213> ORGANISM: Zymomonas mobilis
<220> FEATURE:
<221> NAME/KEY: CDS
<222> LOCATION: (154)..(2328)

<400> SEQUENCE: 1

```
cgatcaccac aattcagcaa attgtgaaca tcatcacgtt catctttccc tggttgccaa        60
tggcccattt tcctgtcagt aacgagaagg tcgcgaattc aggcgctttt tagactggtc       120
gtaatgaaca attcttaaga aggagatata cat atg ggt att gac aga atg aat       174
                                    Met Gly Ile Asp Arg Met Asn
                                      1               5 agc tta agt cgc ttg tta atg aag aag att ttc ggg gct gaa aaa acc       222
Ser Leu Ser Arg Leu Leu Met Lys Lys Ile Phe Gly Ala Glu Lys Thr
         10                  15                  20 tcg tat aaa ccg gct tcc gat acc ata atc gga acg gat acc ctg aaa       270
Ser Tyr Lys Pro Ala Ser Asp Thr Ile Ile Gly Thr Asp Thr Leu Lys
     25                  30                  35 aga ccg aac cgg cgg cct gaa ccg acg gca aaa gtc gac aaa acg ata       318
Arg Pro Asn Arg Arg Pro Glu Pro Thr Ala Lys Val Asp Lys Thr Ile
 40                  45                  50                  55 ttc aag act atg ggg aat agt ctg aat aat acc ctt gtt tca gcc tgt       366
Phe Lys Thr Met Gly Asn Ser Leu Asn Asn Thr Leu Val Ser Ala Cys
                 60                  65                  70 gac tgg ttg atc gga caa caa aag ccc gat ggt cat tgg gtc ggt gcc       414
Asp Trp Leu Ile Gly Gln Gln Lys Pro Asp Gly His Trp Val Gly Ala
             75                  80                  85 gtg gaa tcc aat gct tcg atg gaa gca gaa tgg tgt ctg gcc ttg tgg       462
Val Glu Ser Asn Ala Ser Met Glu Ala Glu Trp Cys Leu Ala Leu Trp
         90                  95                 100 ttt ttg ggt ctg gaa gat cat ccg ctt cgt cca aga ttg ggc aat gct       510
Phe Leu Gly Leu Glu Asp His Pro Leu Arg Pro Arg Leu Gly Asn Ala
105                 110                 115 ctt ttg gaa atg cag cgg gaa gat ggc tct tgg gga gtc tat ttc ggc       558
Leu Leu Glu Met Gln Arg Glu Asp Gly Ser Trp Gly Val Tyr Phe Gly
120                 125                 130                 135 gct gga aat ggc gat atc aat gcc acg gtt gaa gcc tat gcg gcc ttg       606
Ala Gly Asn Gly Asp Ile Asn Ala Thr Val Glu Ala Tyr Ala Ala Leu
                140                 145                 150 cgg tct ttg ggg tat tct gcc gat aat cct gtt ttg aaa aaa gcg gca       654
Arg Ser Leu Gly Tyr Ser Ala Asp Asn Pro Val Leu Lys Lys Ala Ala
            155                 160                 165 gca tgg att gct gaa aaa ggc gga tta aaa aat atc cgt gtc ttt acc       702
Ala Trp Ile Ala Glu Lys Gly Gly Leu Lys Asn Ile Arg Val Phe Thr
        170                 175                 180 cgt tat tgg ctg gcg ttg atc ggg gaa tgg cct tgg gaa aag acc cct       750
Arg Tyr Trp Leu Ala Leu Ile Gly Glu Trp Pro Trp Glu Lys Thr Pro
    185                 190                 195 aac ctt ccc cct gaa att atc tgg ttc cct gat aat ttt gtc ttt tcg       798
Asn Leu Pro Pro Glu Ile Ile Trp Phe Pro Asp Asn Phe Val Phe Ser
200                 205                 210                 215 att tat aat ttt gcc caa tgg gcg cgg gca acc atg gtg ccg att gct       846
Ile Tyr Asn Phe Ala Gln Trp Ala Arg Ala Thr Met Val Pro Ile Ala
                220                 225                 230 att ctg tcc gcg aga cga cca agc cgc ccg ctg cgc cct caa gac cga       894
```

```
Ile Leu Ser Ala Arg Arg Pro Ser Arg Pro Leu Arg Pro Gln Asp Arg
            235                 240                 245 ttg gat gaa ctg ttt cca gaa ggc cgc gct cgc ttt gat tat gaa ttg      942
Leu Asp Glu Leu Phe Pro Glu Gly Arg Ala Arg Phe Asp Tyr Glu Leu
            250                 255                 260 ccg aaa aaa gaa ggc atc gat ctt tgg tcg caa ttt ttc cga acc act      990
Pro Lys Lys Glu Gly Ile Asp Leu Trp Ser Gln Phe Phe Arg Thr Thr
265                 270                 275 gac cgt gga tta cat tgg gtt cag tcc aat ctg tta aag cgc aat agc     1038
Asp Arg Gly Leu His Trp Val Gln Ser Asn Leu Leu Lys Arg Asn Ser
280                 285                 290                 295 ttg cgt gaa gcc gct atc cgt cat gtt ttg gaa tgg att atc cgg cat     1086
Leu Arg Glu Ala Ala Ile Arg His Val Leu Glu Trp Ile Ile Arg His
                300                 305                 310 cag gat gcc gat ggc ggt tgg ggt gga att cag cca cct tgg gtc tat     1134
Gln Asp Ala Asp Gly Gly Trp Gly Gly Ile Gln Pro Pro Trp Val Tyr
                315                 320                 325 ggt ttg atg gcg tta cat ggt gaa ggc tat cag ctt tat cat ccg gtg     1182
Gly Leu Met Ala Leu His Gly Glu Gly Tyr Gln Leu Tyr His Pro Val
                330                 335                 340 atg gcc aag gct ttg tcg gct ttg gat gat ccc ggt tgg cga cat gac     1230
Met Ala Lys Ala Leu Ser Ala Leu Asp Asp Pro Gly Trp Arg His Asp
            345                 350                 355 aga ggc gag tct tct tgg ata cag gcc acc aat agt ccg gta tgg gat     1278
Arg Gly Glu Ser Ser Trp Ile Gln Ala Thr Asn Ser Pro Val Trp Asp
360                 365                 370                 375 aca atg ttg gcc ttg atg gcg tta aaa gac gcc aag gcc gag gat cgt     1326
Thr Met Leu Ala Leu Met Ala Leu Lys Asp Ala Lys Ala Glu Asp Arg
            380                 385                 390 ttt acg ccg gaa atg gat aag gcc gcc gat tgg ctt ttg gct cga cag     1374
Phe Thr Pro Glu Met Asp Lys Ala Ala Asp Trp Leu Leu Ala Arg Gln
            395                 400                 405 gtc aaa gtc aaa ggc gat tgg tca atc aaa ctg ccc gat gtt gaa ccc     1422
Val Lys Val Lys Gly Asp Trp Ser Ile Lys Leu Pro Asp Val Glu Pro
            410                 415                 420 ggt gga tgg gca ttt gaa tat gcc aat gat cgc tat ccc gat acc gat     1470
Gly Gly Trp Ala Phe Glu Tyr Ala Asn Asp Arg Tyr Pro Asp Thr Asp
            425                 430                 435 gat acc gcc gtc gct ttg atc gcc ctt tcc tct tat cgt gat aag gag     1518
Asp Thr Ala Val Ala Leu Ile Ala Leu Ser Ser Tyr Arg Asp Lys Glu
440                 445                 450                 455 gag tgg caa aag aaa ggc gtt gag gac gcc att acc cgt ggg gtt aat     1566
Glu Trp Gln Lys Lys Gly Val Glu Asp Ala Ile Thr Arg Gly Val Asn
                460                 465                 470 tgg ttg atc gcc atg caa agc gaa tgt ggc ggt tgg gga gcc ttt gat     1614
Trp Leu Ile Ala Met Gln Ser Glu Cys Gly Gly Trp Gly Ala Phe Asp
            475                 480                 485 aag gat aat aac aga agt atc ctt tcc aaa att cct ttt tgt gat ttc     1662
Lys Asp Asn Asn Arg Ser Ile Leu Ser Lys Ile Pro Phe Cys Asp Phe
            490                 495                 500 gga gaa tct att gat ccg cct tca gtc gat gta acg gcg cat gtt tta     1710
Gly Glu Ser Ile Asp Pro Pro Ser Val Asp Val Thr Ala His Val Leu
505                 510                 515 gag gcc ttt ggc acc ttg gga ctg tcc cgc gat atg ccg gtc atc caa     1758
Glu Ala Phe Gly Thr Leu Gly Leu Ser Arg Asp Met Pro Val Ile Gln
520                 525                 530                 535 aaa gcg atc gac tat gtc cgt tcc gaa cag gaa gcc gaa ggc gcg tgg     1806
Lys Ala Ile Asp Tyr Val Arg Ser Glu Gln Glu Ala Glu Gly Ala Trp
            540                 545                 550 ttt ggt cgt tgg ggc gtt aat tat atc tat ggc acc ggt gcg gtt ctg     1854
```

|  |  |
|---|---|
| Phe Gly Arg Trp Gly Val Asn Tyr Ile Tyr Gly Thr Gly Ala Val Leu<br>555 560 565 | |
| cct gct ttg gcg gcg atc ggt gaa gat atg acc cag cct tac atc acc<br>Pro Ala Leu Ala Ala Ile Gly Glu Asp Met Thr Gln Pro Tyr Ile Thr<br>570 575 580 | 1902 |
| aag gct tgc gat tgg ctg gtc gca cat cag cag gaa gac ggc ggt tgg<br>Lys Ala Cys Asp Trp Leu Val Ala His Gln Gln Glu Asp Gly Gly Trp<br>585 590 595 | 1950 |
| ggc gaa agc tgc tct tcc tat atg gag att gat tcc att ggg aag ggc<br>Gly Glu Ser Cys Ser Ser Tyr Met Glu Ile Asp Ser Ile Gly Lys Gly<br>600 605 610 615 | 1998 |
| cca acc acg ccg tcc cag act gct tgg gct ttg atg ggg ttg atc gcg<br>Pro Thr Thr Pro Ser Gln Thr Ala Trp Ala Leu Met Gly Leu Ile Ala<br>620 625 630 | 2046 |
| gcc aat cgt ccc gaa gat tat gaa gcc att gcc aag gga tgc cat tat<br>Ala Asn Arg Pro Glu Asp Tyr Glu Ala Ile Ala Lys Gly Cys His Tyr<br>635 640 645 | 2094 |
| ctg att gat cgc caa gag cag gat ggt agc tgg aaa gaa gaa gaa ttc<br>Leu Ile Asp Arg Gln Glu Gln Asp Gly Ser Trp Lys Glu Glu Glu Phe<br>650 655 660 | 2142 |
| acc ggc acc gga ttc ccc ggt tat ggc gtg ggt cag acg atc aag ttg<br>Thr Gly Thr Gly Phe Pro Gly Tyr Gly Val Gly Gln Thr Ile Lys Leu<br>665 670 675 | 2190 |
| gat gat ccg gct tta tcg aaa cga ttg ctt caa ggc gct gaa ctg tca<br>Asp Asp Pro Ala Leu Ser Lys Arg Leu Leu Gln Gly Ala Glu Leu Ser<br>680 685 690 695 | 2238 |
| cgg gcg ttt atg ctg cgt tat gat ttt tat cgg caa ttc ttc ccg att<br>Arg Ala Phe Met Leu Arg Tyr Asp Phe Tyr Arg Gln Phe Phe Pro Ile<br>700 705 710 | 2286 |
| atg gcg tta agt cgg gca gag aga ctg att gat ttg aat aat<br>Met Ala Leu Ser Arg Ala Glu Arg Leu Ile Asp Leu Asn Asn<br>715 720 725 | 2328 |
| tgatagtatt ggggcggagg agtctttta aaagagacta ctccgtccta ttttcgagga | 2388 |
| tccgtcgacc tgcagccaag cttggctgtt ttggcggatg agagaagatt tcagcctga | 2448 |
| tacagattaa atcagaacgc agaagcggtc tgataaaaca gaatttgcct ggcggcagta | 2508 |
| gcgcggtggt cccacctgac cccatgccga actcagaagt gaaacgccgt agcgccgatg | 2568 |
| gtagtgtggg gtctccccat gcgagagtag ggaactgcca ggcatcaaat aaaacgaaag | 2628 |
| gctcagtcga aagactgggc ctttcgtttt atctgttgtt tgtcggtgaa cgctctcctg | 2688 |
| agtaggacaa atccgccggg agcggatttg aacgttgcga agcaacgccc ggagggtgg | 2748 |
| cgggcaggac gcccgccata aactgccagg catcaaatta agcagaaggc catcctgacg | 2808 |
| gatggccttt ttgcgtttct acaaactctt ttgtttattt ttctaaatac attcaaatat | 2868 |
| gtatccgctc atgagacaat aaccctgata aatgcttcaa taatattgaa aaaggaagag | 2928 |
| tatgagtatt caacatttcc gtgtcgccct tattcccttt tttgcggcat tttgccttcc | 2988 |
| tgtttttgct cacccagaaa cgctggtgaa agtaaaagat gctgaagatc agttgggtgc | 3048 |
| acgagtgggt tacatcgaac tggatctcaa cagcggtaag atccttgaga gttttcgccc | 3108 |
| cgaagaacgt tttccaatga tgagcacttt taaagttctg ctatgtggcg cggtattatc | 3168 |
| ccgtgttgac gccgggcaag agcaactcgg tcgccgcata cactattctc agaatgactt | 3228 |
| ggttgagtac tcaccagtca cagaaaagca tcttacggat ggcatgacag taagagaatt | 3288 |
| atgcagtgct gccataacca tgagtgataa cactgcggcc aacttacttc tgacaacgat | 3348 |
| cggaggaccg aaggagctaa ccgcttttt gcacaacatg ggggatcatg taactcgcct | 3408 |
| tgatcgttgg gaaccggagc tgaatgaagc cataccaaac gacgagcgtg acaccacgat | 3468 |

```
gcctgtagca atggcaacaa cgttgcgcaa actattaact ggcgaactac ttactctagc   3528
ttcccggcaa caattaatag actggatgga ggcggataaa gttgcaggac cacttctgcg   3588
ctcggccctt ccggctggct ggtttattgc tgataaatct ggagccggtg agcgtgggtc   3648
tcgcggtatc attgcagcac tggggccaga tggtaagccc tcccgtatcg tagttatcta   3708
cacgacgggg agtcaggcaa ctatggatga acgaaataga cagatcgctg agataggtgc   3768
ctcactgatt aagcattggt aactgtcaga ccaagtttac tcatatatac tttagattga   3828
tttaaaactt cattttttaat ttaaaaggat ctaggtgaag atccttttttg ataatctcat   3888 gaccaaaatc ccttaacgtg agttttcgtt ccactgagcg tcagaccccg tagaaaagat   3948
caaaggatct tcttgagatc cttttttttct gcgcgtaatc tgctgcttgc aaacaaaaaa   4008
accaccgcta ccagcggtgg tttgtttgcc ggatcaagag ctaccaactc tttttccgaa   4068
ggtaactggc ttcagcagag cgcagatacc aaatactgtc cttctagtgt agccgtagtt   4128
aggccaccac ttcaagaact ctgtagcacc gcctacatac ctcgctctgc taatcctgtt   4188
accagtggct gctgccagtg gcgataagtc gtgtcttacc gggttggact caagacgata   4248
gttaccggat aaggcgcagc ggtcgggctg aacggggggt tcgtgcacac agcccagctt   4308
ggagcgaacg acctacaccg aactgagata cctacagcgt gagctatgag aaagcgccac   4368
gcttcccgaa gggagaaagg cggacaggta tccggtaagc ggcagggtcg gaacaggaga   4428
gcgcacgagg gagcttccag ggggaaacgc ctggtatctt tatagtcctg tcgggtttcg   4488
ccacctctga cttgagcgtc gatttttgtg atgctcgtca gggggcgga gcctatggaa   4548 aaacgccagc aacgcggcct ttttacggtt cctggccttt tgctggcctt ttgctcacat   4608
gttctttcct gcgttatccc ctgattctgt ggataaccgt attaccgcct ttgagtgagc   4668
tgataccgct cgccgcagcc gaacgaccga gcgcagcgag tcagtgagcg aggaagcgga   4728
agagcgcctg atgcggtatt ttctccttac gcatctgtgc ggtatttcac accgcatata   4788
tggtgcactc tcagtacaat ctgctctgat gccgcatagt taagccagta tacactccgc   4848
tatcgctacg tgactgggtc atggctgcgc cccgacaccc gccaacaccc gctgacgcgc   4908
cctgacgggc ttgtctgctc ccggcatccg cttacagaca agctgtgacc gtctccggga   4968
gctgcatgtg tcagaggttt tcaccgtcat caccgaaacg cgcgaggcag ctgcggtaaa   5028
gctcatcagc gtggtcgtga agcgattcac agatgtctgc ctgttcatcc gcgtccagct   5088
cgttgagttt ctccagaagc gttaatgtct ggcttctgat aaagcgggcc atgttaaggg   5148
cggttttttc ctgtttggtc actgatgcct ccgtgtaagg gggatttctg ttcatggggg   5208
taatgatacc gatgaaacga gagaggatgc tcacgatacg ggttactgat gatgaacatg   5268
cccggttact ggaacgttgt gagggtaaac aactggcggt atggatgcgg cgggaccaga   5328
gaaaaatcac tcagggtcaa tgccagcgct tcgttaatac agatgtaggt gttccacagg   5388
gtagccagca gcatcctgcg atgcagatcc ggaacataat ggtgcagggc gctgacttcc   5448
gcgtttccag actttacgaa acacggaaac cgaagaccat tcatgttgtt gctcaggtcg   5508
cagacgtttt gcagcagcag tcgcttcacg ttcgctcgcg tatcggtgat tcattctgct   5568
aaccagtaag gcaaccccgc cagcctagcc gggtcctcaa cgacaggagc acgatcatgc   5628
gcacccgtgg ccaggaccca acgctgcccg agatgcgccg cgtgcggctg ctggagatgg   5688
cggacgcgat ggatatgttc tgccaagggt tggtttgcgc attcacagtt ctccgcaaga   5748
attgattggc tccaattctt ggagtggtga atccgttagc gaggtgccgc cggcttccat   5808
tcaggtcgag gtggcccggc tccatgcacc gcgacgcaac gcggggaggc agacaaggta   5868
```

```
tagggcggcg cctacaatcc atgccaaccc gttccatgtg ctcgccgagg cggcataaat      5928
cgccgtgacg atcagcggtc caatgatcga agttaggctg gtaagagccg cgagcgatcc      5988
ttgaagctgt ccctgatggt cgtcatctac ctgcctggac agcatggcct gcaacgcggg      6048
catcccgatg ccgccggaag cgagaagaat cataatgggg aaggccatcc agcctcgcgt      6108
cgcgaacgcc agcaagacgt agcccagcgc gtcggccgcc atgccggcga taatggcctg      6168
cttctcgccg aaacgtttgg tggcgggacc agtgacgaag gcttgagcga gggcgtgcaa      6228
gattccgaat accgcaagcg acaggccgat catcgtcgcg ctccagcgaa agcggtcctc      6288
gccgaaaatg acccagagcg ctgccggcac ctgtcctacg agttgcatga taaagaagac      6348
agtcataagt gcggcgacga tagtcatgcc ccgcgcccac cggaaggagc tgactgggtt      6408
gaaggctctc aagggcatcg gtcgacgctc tcccttatgc gactcctgca ttaggaagca      6468
gcccagtagt aggttgaggc cgttgagcac cgccgccgca aggaatggtg catgcat         6525
```

<210> SEQ ID NO 2
<211> LENGTH: 725
<212> TYPE: PRT
<213> ORGANISM: Zymomonas mobilis

<400> SEQUENCE: 2

```
Met Gly Ile Asp Arg Met Asn Ser Leu Ser Arg Leu Leu Met Lys Lys
1               5                   10                  15

Ile Phe Gly Ala Glu Lys Thr Ser Tyr Lys Pro Ala Ser Asp Thr Ile
            20                  25                  30

Ile Gly Thr Asp Thr Leu Lys Arg Pro Asn Arg Arg Pro Glu Pro Thr
        35                  40                  45

Ala Lys Val Asp Lys Thr Ile Phe Lys Thr Met Gly Asn Ser Leu Asn
    50                  55                  60

Asn Thr Leu Val Ser Ala Cys Asp Trp Leu Ile Gly Gln Gln Lys Pro
65                  70                  75                  80

Asp Gly His Trp Val Gly Ala Val Glu Ser Asn Ala Ser Met Glu Ala
                85                  90                  95

Glu Trp Cys Leu Ala Leu Trp Phe Leu Gly Leu Glu Asp His Pro Leu
            100                 105                 110

Arg Pro Arg Leu Gly Asn Ala Leu Leu Glu Met Gln Arg Glu Asp Gly
        115                 120                 125

Ser Trp Gly Val Tyr Phe Gly Ala Gly Asn Gly Asp Ile Asn Ala Thr
    130                 135                 140

Val Glu Ala Tyr Ala Ala Leu Arg Ser Leu Gly Tyr Ser Ala Asp Asn
145                 150                 155                 160

Pro Val Leu Lys Lys Ala Ala Ala Trp Ile Ala Glu Lys Gly Gly Leu
                165                 170                 175

Lys Asn Ile Arg Val Phe Thr Arg Tyr Trp Leu Ala Leu Ile Gly Glu
            180                 185                 190

Trp Pro Trp Glu Lys Thr Pro Asn Leu Pro Pro Glu Ile Ile Trp Phe
        195                 200                 205

Pro Asp Asn Phe Val Phe Ser Ile Tyr Asn Phe Ala Gln Trp Ala Arg
    210                 215                 220

Ala Thr Met Val Pro Ile Ala Ile Leu Ser Ala Arg Arg Pro Ser Arg
225                 230                 235                 240

Pro Leu Arg Pro Gln Asp Arg Leu Asp Glu Leu Phe Pro Glu Gly Arg
                245                 250                 255

Ala Arg Phe Asp Tyr Glu Leu Pro Lys Lys Glu Gly Ile Asp Leu Trp
```

-continued

```
                260                 265                 270
Ser Gln Phe Phe Arg Thr Thr Asp Arg Gly Leu His Trp Val Gln Ser
            275                 280                 285

Asn Leu Leu Lys Arg Asn Ser Leu Arg Glu Ala Ala Ile Arg His Val
        290                 295                 300

Leu Glu Trp Ile Ile Arg His Gln Asp Ala Asp Gly Gly Trp Gly Gly
305                 310                 315                 320

Ile Gln Pro Pro Trp Val Tyr Gly Leu Met Ala Leu His Gly Glu Gly
                325                 330                 335

Tyr Gln Leu Tyr His Pro Val Met Ala Lys Ala Leu Ser Ala Leu Asp
            340                 345                 350

Asp Pro Gly Trp Arg His Asp Arg Gly Glu Ser Ser Trp Ile Gln Ala
        355                 360                 365

Thr Asn Ser Pro Val Trp Asp Thr Met Leu Ala Leu Met Ala Leu Lys
    370                 375                 380

Asp Ala Lys Ala Glu Asp Arg Phe Thr Pro Glu Met Asp Lys Ala Ala
385                 390                 395                 400

Asp Trp Leu Leu Ala Arg Gln Val Lys Val Lys Gly Asp Trp Ser Ile
                405                 410                 415

Lys Leu Pro Asp Val Glu Pro Gly Gly Trp Ala Phe Glu Tyr Ala Asn
            420                 425                 430

Asp Arg Tyr Pro Asp Thr Asp Thr Ala Val Ala Leu Ile Ala Leu
        435                 440                 445

Ser Ser Tyr Arg Asp Lys Glu Glu Trp Gln Lys Lys Gly Val Glu Asp
    450                 455                 460

Ala Ile Thr Arg Gly Val Asn Trp Leu Ile Ala Met Gln Ser Glu Cys
465                 470                 475                 480

Gly Gly Trp Gly Ala Phe Asp Lys Asp Asn Asn Arg Ser Ile Leu Ser
                485                 490                 495

Lys Ile Pro Phe Cys Asp Phe Gly Glu Ser Ile Asp Pro Pro Ser Val
            500                 505                 510

Asp Val Thr Ala His Val Leu Glu Ala Phe Gly Thr Leu Gly Leu Ser
        515                 520                 525

Arg Asp Met Pro Val Ile Gln Lys Ala Ile Asp Tyr Val Arg Ser Glu
    530                 535                 540

Gln Glu Ala Glu Gly Ala Trp Phe Gly Arg Trp Gly Val Asn Tyr Ile
545                 550                 555                 560

Tyr Gly Thr Gly Ala Val Leu Pro Ala Leu Ala Ala Ile Gly Glu Asp
                565                 570                 575

Met Thr Gln Pro Tyr Ile Thr Lys Ala Cys Asp Trp Leu Val Ala His
            580                 585                 590

Gln Gln Glu Asp Gly Gly Trp Gly Glu Ser Cys Ser Ser Tyr Met Glu
        595                 600                 605

Ile Asp Ser Ile Gly Lys Gly Pro Thr Thr Pro Ser Gln Thr Ala Trp
    610                 615                 620

Ala Leu Met Gly Leu Ile Ala Ala Asn Arg Pro Glu Asp Tyr Glu Ala
625                 630                 635                 640

Ile Ala Lys Gly Cys His Tyr Leu Ile Asp Arg Gln Glu Gln Asp Gly
                645                 650                 655

Ser Trp Lys Glu Glu Phe Thr Gly Thr Gly Phe Pro Gly Tyr Gly
            660                 665                 670

Val Gly Gln Thr Ile Lys Leu Asp Asp Pro Ala Leu Ser Lys Arg Leu
        675                 680                 685
```

Leu Gln Gly Ala Glu Leu Ser Arg Ala Phe Met Leu Arg Tyr Asp Phe
        690                 695                 700

Tyr Arg Gln Phe Phe Pro Ile Met Ala Leu Ser Arg Ala Glu Arg Leu
705                 710                 715                 720

Ile Asp Leu Asn Asn
            725

<210> SEQ ID NO 3
<211> LENGTH: 25
<212> TYPE: DNA
<213> ORGANISM: Artificial Sequence
<220> FEATURE:
<223> OTHER INFORMATION: Primer

<400> SEQUENCE: 3
gcgctgtttc atatgggtat tgaca                                        25

<210> SEQ ID NO 4
<211> LENGTH: 25
<212> TYPE: DNA
<213> ORGANISM: Artificial Sequence
<220> FEATURE:
<223> OTHER INFORMATION: Primer

<400> SEQUENCE: 4
gcgcttaccc tggatcctcg aaaat                                        25

<210> SEQ ID NO 5
<211> LENGTH: 684
<212> TYPE: PRT
<213> ORGANISM: Bradyrhizobium japonicum

<400> SEQUENCE: 5

Met Thr Val Thr Ser Ala Ser Ala Arg Ala Thr Arg Asp Pro Gly
1               5                   10                  15

Asn Tyr Gln Thr Ala Leu Gln Ser Thr Val Arg Ala Ala Asp Trp
            20                  25                  30

Leu Ile Ala Asn Gln Lys Pro Asp Gly His Trp Val Gly Arg Ala Glu
        35                  40                  45

Ser Asn Ala Cys Met Glu Ala Gln Trp Cys Leu Ala Leu Trp Phe Met
    50                  55                  60

Gly Leu Glu Asp His Pro Leu Arg Lys Arg Leu Gly Gln Ser Leu Leu
65                  70                  75                  80

Asp Ser Gln Arg Pro Asp Gly Ala Trp Gln Val Tyr Phe Gly Ala Pro
                85                  90                  95

Asn Gly Asp Ile Asn Ala Thr Val Glu Ala Tyr Ala Ala Leu Arg Ser
            100                 105                 110

Leu Gly Phe Arg Asp Asp Glu Pro Ala Val Arg Arg Ala Arg Glu Trp
        115                 120                 125

Ile Glu Ala Lys Gly Gly Leu Arg Asn Ile Arg Val Phe Thr Arg Tyr
    130                 135                 140

Trp Leu Ala Leu Ile Gly Glu Trp Pro Trp Glu Lys Thr Pro Asn Ile
145                 150                 155                 160

Pro Pro Glu Val Ile Trp Phe Pro Leu Trp Phe Pro Phe Ser Ile Tyr
                165                 170                 175

Asn Phe Ala Gln Trp Ala Arg Ala Thr Leu Met Pro Ile Ala Val Leu
            180                 185                 190

Ser Ala Arg Arg Pro Ser Arg Pro Leu Pro Pro Glu Asn Arg Leu Asp
        195                 200                 205

```
Ala Leu Phe Pro His Gly Arg Lys Ala Phe Asp Tyr Glu Leu Pro Val
    210                 215                 220

Lys Ala Gly Ala Gly Trp Asp Arg Phe Arg Gly Ala Asp Lys
225                 230                 235                 240

Val Leu His Lys Leu Gln Asn Leu Gly Asn Arg Leu Asn Leu Gly Leu
                245                 250                 255

Phe Arg Pro Ala Ala Thr Ser Arg Val Leu Glu Trp Met Ile Arg His
            260                 265                 270

Gln Asp Phe Asp Gly Ala Trp Gly Gly Ile Gln Pro Trp Ile Tyr
        275                 280                 285

Gly Leu Met Ala Leu Tyr Ala Glu Gly Tyr Pro Leu Asn His Pro Val
    290                 295                 300

Leu Ala Lys Gly Leu Asp Ala Leu Asn Asp Pro Gly Trp Arg Val Asp
305                 310                 315                 320

Val Gly Asp Ala Thr Tyr Ile Gln Ala Thr Asn Ser Pro Val Trp Asp
                325                 330                 335

Thr Ile Leu Thr Leu Leu Ala Phe Asp Asp Ala Gly Val Leu Gly Asp
            340                 345                 350

Tyr Pro Glu Ala Val Asp Lys Ala Val Asp Trp Val Leu Gln Arg Gln
        355                 360                 365

Val Arg Val Pro Gly Asp Trp Ser Met Lys Leu Pro His Val Lys Pro
    370                 375                 380

Gly Gly Trp Ala Phe Glu Tyr Ala Asn Asn Tyr Tyr Pro Asp Thr Asp
385                 390                 395                 400

Asp Thr Ala Val Ala Leu Ile Ala Leu Ala Pro Leu Arg His Asp Pro
                405                 410                 415

Lys Trp Lys Ala Lys Gly Ile Asp Glu Ala Ile Gln Leu Gly Val Asp
            420                 425                 430

Trp Leu Ile Gly Met Gln Ser Gln Gly Gly Trp Gly Ala Phe Asp
        435                 440                 445

Lys Asp Asn Asn Gln Lys Ile Leu Thr Lys Ile Pro Phe Cys Asp Tyr
        450                 455                 460

Gly Glu Ala Leu Asp Pro Pro Ser Val Asp Val Thr Ala His Ile Ile
465                 470                 475                 480

Glu Ala Phe Gly Lys Leu Gly Ile Ser Arg Asn His Pro Ser Met Val
                485                 490                 495

Gln Ala Leu Asp Tyr Ile Arg Arg Glu Gln Glu Pro Ser Gly Pro Trp
            500                 505                 510

Phe Gly Arg Trp Gly Val Asn Tyr Val Tyr Gly Thr Gly Ala Val Leu
        515                 520                 525

Pro Ala Leu Ala Ala Ile Gly Glu Asp Met Thr Gln Pro Tyr Ile Gly
    530                 535                 540

Arg Ala Cys Asp Trp Leu Val Ala His Gln Gln Ala Asp Gly Gly Trp
545                 550                 555                 560

Gly Glu Ser Cys Ala Ser Tyr Met Asp Val Ser Ala Val Gly Arg Gly
                565                 570                 575

Thr Thr Thr Ala Ser Gln Thr Ala Trp Ala Leu Met Ala Leu Leu Ala
            580                 585                 590

Ala Asn Arg Pro Gln Asp Lys Asp Ala Ile Glu Arg Gly Cys Met Trp
        595                 600                 605

Leu Val Glu Arg Gln Ser Ala Gly Thr Trp Asp Glu Pro Glu Phe Thr
    610                 615                 620

Gly Thr Gly Phe Pro Gly Tyr Gly Val Gly Gln Thr Ile Lys Leu Asn
625                 630                 635                 640
```

```
Asp Pro Ala Leu Ser Gln Arg Leu Met Gln Gly Pro Glu Leu Ser Arg
                645                 650                 655

Ala Phe Met Leu Arg Tyr Gly Met Tyr Arg His Tyr Phe Pro Leu Met
            660                 665                 670

Ala Leu Gly Arg Ala Leu Arg Pro Gln Ser His Ser
        675                 680
```

<210> SEQ ID NO 6
<211> LENGTH: 657
<212> TYPE: PRT
<213> ORGANISM: Burkholderia ambifaria

<400> SEQUENCE: 6

```
Met Asn Asp Leu Thr Glu Met Ala Thr Leu Ser Ala Gly Thr Val Pro
1               5                   10                  15

Ala Gly Leu Asp Ala Ala Val Ala Ser Ala Thr Asp Ala Leu Leu Ala
            20                  25                  30

Ala Gln Asn Ala Asp Gly His Trp Val Tyr Glu Leu Glu Ala Asp Ser
        35                  40                  45

Thr Ile Pro Ala Glu Tyr Val Leu Leu Val His Tyr Leu Gly Glu Thr
50                  55                  60

Pro Asn Leu Glu Leu Glu Gln Lys Ile Gly Arg Tyr Leu Arg Arg Val
65                  70                  75                  80

Gln Gln Ala Asp Gly Gly Trp Pro Leu Phe Thr Asp Gly Ala Pro Asn
                85                  90                  95

Ile Ser Ala Ser Val Lys Ala Tyr Phe Ala Leu Lys Val Ile Gly Asp
            100                 105                 110

Asp Glu Asn Ala Glu His Met Gln Arg Ala Arg Arg Ala Ile Gln Ala
        115                 120                 125

Met Gly Gly Ala Glu Met Ser Asn Val Phe Thr Arg Ile Gln Leu Ala
    130                 135                 140

Leu Tyr Gly Ala Ile Pro Trp Arg Ala Val Pro Met Met Pro Val Glu
145                 150                 155                 160

Ile Met Leu Leu Pro Gln Trp Phe Pro Phe His Leu Ser Lys Val Ser
                165                 170                 175

Tyr Trp Ala Arg Thr Val Ile Val Pro Leu Leu Val Leu Asn Ala Lys
            180                 185                 190

Arg Pro Ile Ala Lys Asn Pro Arg Gly Val Arg Ile Asp Glu Leu Phe
        195                 200                 205

Val Asp Pro Pro Val Asn Ala Gly Leu Leu Pro Arg Gln Gly His Gln
    210                 215                 220

Ser Pro Gly Trp Phe Ala Phe Phe Arg Val Val Asp His Ala Leu Arg
225                 230                 235                 240

Ala Ala Asp Gly Leu Phe Pro Asn Tyr Thr Arg Glu Arg Ala Ile Arg
                245                 250                 255

Gln Ala Val Ser Phe Val Asp Glu Arg Leu Asn Gly Glu Asp Gly Leu
            260                 265                 270

Gly Ala Ile Tyr Pro Ala Met Ala Asn Ala Val Met Met Tyr Asp Val
        275                 280                 285

Leu Gly Tyr Ala Glu Asp His Pro Asn Arg Ala Ile Ala Arg Lys Ser
    290                 295                 300

Ile Glu Lys Leu Leu Val Val Gln Glu Asp Glu Ala Tyr Cys Gln Pro
305                 310                 315                 320

Cys Leu Ser Pro Val Trp Asp Thr Ser Leu Ala Ala His Ala Leu Leu
                325                 330                 335
```

```
Glu Thr Gly Asp Ala Arg Ala Glu Ala Val Ile Arg Gly Leu Glu
            340                 345                 350

Trp Leu Arg Pro Leu Gln Ile Leu Asp Val Arg Gly Asp Trp Ile Ser
        355                 360                 365

Arg Arg Pro His Val Arg Pro Gly Gly Trp Ala Phe Gln Tyr Ala Asn
    370                 375                 380

Pro His Tyr Pro Asp Val Asp Thr Ala Val Val Ala Val Ala Met
385                 390                 395                 400

Asp Arg Val Gln Lys Leu Lys His Asn Asp Ala Phe Arg Asp Ser Ile
                405                 410                 415

Ala Arg Ala Arg Glu Trp Val Val Gly Met Gln Ser Ser Asp Gly Gly
            420                 425                 430

Trp Gly Ala Phe Glu Pro Glu Asn Thr Gln Tyr Tyr Leu Asn Asn Ile
        435                 440                 445

Pro Phe Ser Asp His Gly Ala Leu Leu Asp Pro Pro Thr Ala Asp Val
    450                 455                 460

Ser Gly Arg Cys Leu Ser Met Leu Ala Gln Leu Gly Glu Thr Pro Leu
465                 470                 475                 480

Asn Ser Glu Pro Ala Arg Arg Ala Leu Asp Tyr Met Leu Lys Glu Gln
                485                 490                 495

Glu Pro Asp Gly Ser Trp Tyr Gly Arg Trp Gly Met Asn Tyr Val Tyr
            500                 505                 510

Gly Thr Trp Thr Ala Leu Cys Ala Leu Asn Ala Ala Gly Leu Thr Pro
        515                 520                 525

Asp Asp Pro Arg Val Lys Arg Gly Ala Gln Trp Leu Leu Ser Ile Gln
    530                 535                 540

Asn Lys Asp Gly Gly Trp Gly Glu Asp Gly Asp Ser Tyr Lys Leu Asn
545                 550                 555                 560

Tyr Arg Gly Phe Glu Gln Ala Pro Ser Thr Ala Ser Gln Thr Ala Trp
                565                 570                 575

Ala Leu Leu Gly Leu Met Ala Ala Gly Glu Val Asn Asn Pro Ala Val
            580                 585                 590

Ala Arg Gly Val Glu Tyr Leu Ile Ala Glu Gln Lys Glu His Gly Leu
        595                 600                 605

Trp Asp Glu Thr Arg Phe Thr Ala Thr Gly Phe Pro Arg Val Phe Tyr
    610                 615                 620

Leu Arg Tyr His Gly Tyr Arg Lys Phe Phe Pro Leu Trp Ala Leu Ala
625                 630                 635                 640

Arg Tyr Arg Asn Leu Lys Arg Asn Asn Ala Thr Arg Val Thr Phe Gly
                645                 650                 655

Leu

<210> SEQ ID NO 7
<211> LENGTH: 682
<212> TYPE: PRT
<213> ORGANISM: Burkholderia ambifaria

<400> SEQUENCE: 7

Met Ile Arg Arg Met Asn Lys Ser Gly Pro Ser Pro Trp Ser Ala Leu
1               5                   10                  15

Asp Ala Ala Ile Ala Arg Gly Arg Asp Ala Leu Met Arg Leu Gln Gln
            20                  25                  30

Pro Asp Gly Ser Trp Cys Phe Glu Leu Glu Ser Asp Ala Thr Ile Thr
        35                  40                  45
```

```
Ala Glu Tyr Ile Leu Met Met His Phe Met Asp Lys Ile Asp Asp Ala
 50                  55                  60

Arg Gln Glu Lys Met Ala Arg Tyr Leu Arg Ala Ile Gln Arg Leu Asp
 65                  70                  75                  80

Thr His Gly Gly Trp Asp Leu Tyr Val Asp Gly Asp Pro Asp Val Ser
                     85                  90                  95

Cys Ser Val Lys Ala Tyr Phe Ala Leu Lys Ala Ala Gly Asp Ser Glu
                100                 105                 110

His Ala Pro His Met Val Arg Ala Arg Asp Ala Ile Leu Glu Leu Gly
            115                 120                 125

Gly Ala Ala Arg Ser Asn Val Phe Thr Arg Ile Leu Leu Ala Thr Phe
130                 135                 140

Gly Gln Val Pro Trp Arg Ala Thr Pro Phe Met Pro Ile Glu Phe Val
145                 150                 155                 160

Leu Phe Pro Lys Trp Val Pro Ile Ser Met Tyr Lys Val Ala Tyr Trp
                165                 170                 175

Ala Arg Thr Thr Met Val Pro Leu Leu Val Leu Cys Ser Leu Lys Ala
                180                 185                 190

Arg Ala Arg Asn Pro Arg Asn Ile Ala Ile Pro Glu Leu Phe Val Thr
            195                 200                 205

Pro Pro Asp Gln Glu Arg Gln Tyr Phe Pro Pro Ala Arg Gly Met Arg
210                 215                 220

Arg Ala Phe Leu Ala Leu Asp Arg Val Val Arg His Val Glu Pro Leu
225                 230                 235                 240

Leu Pro Lys Arg Leu Arg Gln Arg Ala Ile Arg His Ala Gln Ala Trp
                245                 250                 255

Cys Ala Glu Arg Met Asn Gly Glu Asp Gly Leu Gly Gly Ile Phe Pro
                260                 265                 270

Pro Ile Val Tyr Ser Tyr Gln Met Met Asp Val Leu Gly Tyr Pro Asp
            275                 280                 285

Asp His Pro Leu Arg Arg Asp Cys Glu Asn Ala Leu Glu Lys Leu Leu
        290                 295                 300

Val Thr Arg Pro Asp Gly Ser Met Tyr Cys Gln Pro Cys Leu Ser Pro
305                 310                 315                 320

Val Trp Asp Thr Ala Trp Ser Thr Met Ala Leu Glu Gln Ala Arg Gly
                325                 330                 335

Val Ala Val Pro Glu Ala Gly Ala Pro Ala Ser Ala Leu Asp Glu Leu
                340                 345                 350

Asp Ala Arg Ile Ala Arg Ala Tyr Asp Trp Leu Ala Glu Arg Gln Val
            355                 360                 365

Asn Asp Leu Arg Gly Asp Trp Ile Glu Asn Ala Pro Ala Asp Thr Gln
        370                 375                 380

Pro Gly Gly Trp Ala Phe Gln Tyr Ala Asn Pro Tyr Tyr Pro Asp Ile
385                 390                 395                 400

Asp Asp Ser Ala Val Val Thr Ala Met Leu Asp Arg Arg Gly Arg Thr
                405                 410                 415

His Arg Asn Ala Asp Gly Ser His Pro Tyr Ala Ala Arg Val Ala Arg
                420                 425                 430

Ala Leu Asp Trp Met Arg Gly Leu Gln Ser Arg Asn Gly Phe Ala
            435                 440                 445

Ala Phe Asp Ala Asp Cys Asp Arg Leu Tyr Leu Asn Ala Ile Pro Phe
        450                 455                 460

Ala Asp His Gly Ala Leu Leu Asp Pro Pro Thr Glu Asp Val Ser Gly
465                 470                 475                 480
```

```
Arg Val Leu Leu Cys Phe Gly Val Thr Lys Arg Ala Asp Arg Ala
                485                 490                 495

Ser Leu Ala Arg Ala Ile Asp Tyr Val Lys Arg Thr Gln Gln Pro Asp
            500                 505                 510

Gly Ser Trp Trp Gly Arg Trp Gly Thr Asn Tyr Leu Tyr Gly Thr Trp
            515                 520                 525

Ser Val Leu Ala Gly Leu Ala Leu Ala Gly Glu Asp Pro Ser Gln Pro
        530                 535                 540

Tyr Ile Ala Arg Ala Leu Ala Trp Leu Arg Ala Arg Gln His Ala Asp
545                 550                 555                 560

Gly Gly Trp Gly Glu Thr Asn Asp Ser Tyr Ile Asp Pro Ala Leu Ala
                565                 570                 575

Gly Thr Asn Ala Gly Glu Ser Thr Ser Asn Cys Thr Ala Trp Ala Leu
            580                 585                 590

Leu Ala Gln Met Ala Phe Gly Asp Gly Glu Ser Glu Ser Val Arg Arg
        595                 600                 605

Gly Ile Ala Tyr Leu Gln Ser Val Gln Gln Asp Asp Gly Phe Trp Trp
610                 615                 620

His Arg Ser His Asn Ala Pro Gly Phe Pro Arg Ile Phe Tyr Leu Lys
625                 630                 635                 640

Tyr His Gly Tyr Thr Ala Tyr Phe Pro Leu Trp Ala Leu Ala Arg Tyr
                645                 650                 655

Arg Arg Leu Ala Gly Gly Val Ser Ala Ala Gly Ala His Ala Val Pro
            660                 665                 670

Ala Ser Thr Gly Ala Asp Ala Ala Leu Ala
            675                 680

<210> SEQ ID NO 8
<211> LENGTH: 617
<212> TYPE: PRT
<213> ORGANISM: Bacillus anthracis

<400> SEQUENCE: 8

Met Leu Leu Tyr Glu Lys Ala His Glu Glu Ile Val Arg Arg Ala Thr
1               5                   10                  15

Ala Leu Gln Thr Met Gln Trp Gln Asp Gly Thr Trp Arg Phe Cys Phe
            20                  25                  30

Glu Gly Ala Pro Leu Thr Asp Cys His Met Ile Phe Leu Leu Lys Leu
        35                  40                  45

Leu Gly Arg Asp Lys Glu Ile Glu Pro Phe Val Glu Arg Val Ala Ser
    50                  55                  60

Leu Gln Thr Asn Glu Gly Thr Trp Lys Leu His Glu Asp Glu Val Gly
65                  70                  75                  80

Gly Asn Leu Ser Ala Thr Ile Gln Ser Tyr Ala Ala Leu Leu Ala Ser
                85                  90                  95

Lys Lys Tyr Thr Lys Glu Asp Ala Asn Met Lys Arg Ala Glu Asn Phe
            100                 105                 110

Ile Gln Glu Arg Gly Gly Val Ala Arg Ala His Phe Met Thr Lys Phe
        115                 120                 125

Leu Leu Ala Ile His Gly Glu Tyr Glu Tyr Pro Ser Leu Phe His Leu
    130                 135                 140

Pro Thr Pro Ile Met Phe Leu Gln Asn Asp Ser Pro Phe Ser Ile Phe
145                 150                 155                 160

Glu Leu Ser Ser Ser Ala Arg Ile His Leu Ile Pro Met Met Leu Cys
                165                 170                 175
```

-continued

```
Leu Asn Lys Arg Phe Arg Val Gly Lys Lys Leu Leu Pro Asn Leu Asn
            180                 185                 190

His Ile Ala Gly Gly Gly Glu Trp Phe Arg Glu Asp Arg Ser Pro
        195                 200                 205

Val Phe Gln Thr Leu Leu Ser Asp Val Lys Gln Ile Ile Ser Tyr Pro
    210                 215                 220

Leu Ser Leu His His Lys Gly Tyr Glu Glu Ile Glu Arg Phe Met Lys
225                 230                 235                 240

Glu Arg Ile Asp Glu Asn Gly Thr Leu Tyr Ser Tyr Ala Thr Ala Ser
                245                 250                 255

Phe Tyr Met Ile Tyr Ala Leu Leu Ala Leu Gly His Ser Leu Gln Ser
            260                 265                 270

Ser Met Ile Gln Lys Ala Ile Ala Gly Ile Thr Ser Tyr Ile Trp Lys
        275                 280                 285

Met Glu Arg Gly Asn His Leu Gln Asn Ser Pro Ser Thr Val Trp Asp
    290                 295                 300

Thr Ala Leu Leu Ser Tyr Ala Leu Gln Glu Ala Gln Val Ser Lys Asp
305                 310                 315                 320

Asn Lys Met Ile Gln Asn Ala Thr Ala Tyr Leu Leu Lys Lys Gln His
                325                 330                 335

Thr Lys Lys Ala Asp Trp Ser Val His Ala Pro Ala Leu Thr Pro Gly
            340                 345                 350

Gly Trp Gly Phe Ser Asp Val Asn Thr Thr Ile Pro Asp Ile Asp Asp
        355                 360                 365

Thr Thr Ala Val Leu Arg Ala Leu Ala Arg Ser Arg Gly Asn Lys Asn
    370                 375                 380

Ile Asp Asn Ala Trp Lys Lys Gly Gly Asn Trp Ile Lys Gly Leu Gln
385                 390                 395                 400

Asn Asn Asp Gly Gly Trp Gly Ala Phe Glu Lys Gly Val Thr Ser Lys
                405                 410                 415

Leu Leu Ala Lys Leu Pro Ile Glu Asn Ala Ser Asp Met Ile Thr Asp
            420                 425                 430

Pro Ser Thr Pro Asp Ile Thr Gly Arg Val Leu Glu Phe Phe Gly Thr
        435                 440                 445

Tyr Ala Gln Asn Glu Leu Pro Glu Lys Gln Ile Gln Arg Ala Ile Asn
    450                 455                 460

Trp Leu Met Asn Val Gln Glu Asn Gly Ser Trp Tyr Gly Lys Trp
465                 470                 475                 480

Gly Ile Cys Tyr Leu Tyr Gly Thr Trp Ala Val Met Thr Gly Leu Arg
                485                 490                 495

Ser Leu Gly Ile Pro Ser Ser Asn Pro Ser Leu Thr Arg Ala Ala Ser
            500                 505                 510

Trp Leu Glu His Ile Gln His Glu Asp Gly Gly Trp Gly Glu Ser Cys
        515                 520                 525

His Ser Ser Val Glu Lys Arg Phe Val Thr Leu Pro Phe Ser Thr Pro
    530                 535                 540

Ser Gln Thr Ala Trp Ala Leu Asp Ala Leu Ile Ser Tyr Tyr Asp Thr
545                 550                 555                 560

Glu Thr Pro Ala Ile Arg Lys Gly Val Ser Tyr Leu Leu Ser Asn Pro
                565                 570                 575

Tyr Val Asn Glu Arg Tyr Pro Thr Gly Thr Gly Leu Pro Gly Ala Phe
            580                 585                 590

Tyr Ile Arg Tyr His Ser Tyr Ala His Ile Tyr Pro Leu Leu Thr Leu
```

```
                    595                 600                 605
Ala His Tyr Ile Lys Lys Tyr Arg Lys
    610                 615

<210> SEQ ID NO 9
<211> LENGTH: 720
<212> TYPE: PRT
<213> ORGANISM: Frankia alni

<400> SEQUENCE: 9

Met Pro Ala Gly Val Gly Val Leu Val Trp Leu Asp Gln Arg Leu Arg
1               5                   10                  15

Ala Met Gly Arg Pro Asp Leu Val Thr Thr Gly Ala Glu Ile
            20                  25                  30

Pro Phe Val Leu Val Ala Thr Ala Ser Thr Val Gly Val Ala Leu
        35                  40                  45

Ala Leu Arg Arg Pro Arg His Pro Val Gly Trp Leu Phe Leu Ala Leu
    50                  55                  60

Gly Gly Val Leu Leu Ser Gly Gly Thr Gln Gly Tyr Ala Ala Tyr
65                  70                  75                  80

Gly Ala Val Ala Arg Pro Gly Arg Leu Pro Ala Ala Asp Leu Val Ala
                85                  90                  95

Ile Tyr Ala Asp Ala Gly Phe Ile Pro Trp Leu Val Leu Val Ala Leu
            100                 105                 110

Ile Leu His Leu Thr Pro Thr Gly Arg Pro Leu Ser Ala Arg Trp Gly
        115                 120                 125

Arg Ile Ala Leu Ala Thr Ala Val Ala Gly Gly Leu Trp Leu Leu Val
    130                 135                 140

Gly Leu Val Thr Thr Glu Thr Met Gln Pro Pro Phe Gln Ser Val Thr
145                 150                 155                 160

Asn Pro Leu Leu Ile Gly Gly Pro Leu Gly Pro Leu Val Ala Arg
                165                 170                 175

Arg Val Leu Gly Leu Ala Thr Gly Ala Gly Val Val Leu Ala Ala Val
            180                 185                 190

Ser Leu Ile Val Arg Phe Arg Arg Ser Val Asp Val Glu Arg Arg Gln
        195                 200                 205

Leu Leu Trp Val Ala Val Ala Ala Val Pro Leu Pro Val Leu Met Ala
    210                 215                 220

Ala Ser Phe Ala Ala Ser Tyr Ala Gly Asn Asn Thr Ala Ala Gly Leu
225                 230                 235                 240

Ala Ala Ala Thr Leu Ile Gly Leu Leu Ala Ile Gly Ala Gly Leu Ala
                245                 250                 255

Ile Gly Gln Tyr His Leu Tyr Asp Val Glu Glu Ile Leu Ser Arg Ala
            260                 265                 270

Val Thr Tyr Leu Leu Val Ser Gly Leu Leu Ala Ala Ser Tyr Ala Thr
        275                 280                 285

Val Val Ile Val Val Gly Gln Ser Leu Ala Gly Arg Thr Gly Arg Ser
    290                 295                 300

Gln Ile Ser Ala Val Leu Ala Thr Leu Ala Ala Val Ala Val Thr Ala
305                 310                 315                 320

Pro Ala Tyr Arg Lys Ile Gln Glu Gly Val Asp Arg Arg Phe Ser Arg
                325                 330                 335

Arg Arg Phe Glu Thr Leu Gln Val Ile Arg Arg Tyr Leu Arg Asp Pro
            340                 345                 350

Asp Pro Asp Val Ala Val Glu Glu Val Leu Arg Arg Ala Leu Gly Asp
```

```
                355                 360                 365
Pro Thr Leu Ala Val Ala Tyr Leu Val Asp Asp Arg Arg Gln Trp Val
370                 375                 380

Ser Ala Asp Gly Gln Pro Ala Asn Pro Gly Asn Ser Phe Met Ala Ala
385                 390                 395                 400

Val Glu Val Tyr Arg Arg Gly Arg Pro Ile Ala Arg Val Thr Phe Asp
                405                 410                 415

Arg Gly Arg Ala Gln Pro Gly Leu Val Arg Ala Ala Thr Ala Ala
        420                 425                 430

Thr Ala Glu Leu Asp Asn Ala Gly Leu Arg Ala Ala Val Ala Leu Gln
                435                 440                 445

Leu Val Glu Val Arg Gln Ser Arg Thr Arg Ile Ala Ala Gln Phe
450                 455                 460

Ala Glu Arg Arg Thr Ile Glu Arg Asn Leu His Asp Gly Ala Gln Gln
465                 470                 475                 480

Arg Leu Leu Ala Leu Ala Leu Gln Leu Arg Ala Val Gln Leu Gly Gly
                485                 490                 495

Asp Glu Ala Ser Leu Arg Gln Ala Ile Ser Thr Gly Ile Asp Gln Leu
                500                 505                 510

Gln Ala Ala Val Val Glu Leu Arg Glu Leu Ala Asn Gly Leu His Pro
515                 520                 525

Ala Val Leu Ala Asp Gly Gly Leu Ala Ala Ala Leu Asp Asp Val Ala
                530                 535                 540

Ala Arg Thr Pro Val Pro Ile Lys Ile Ser Ala Pro Asp Arg Arg Tyr
545                 550                 555                 560

Pro Pro Asp Leu Glu Ala Ala Ala Trp Phe Ile Ala Cys Glu Ala Met
                565                 570                 575

Ala Asn Ala Val Lys His Ala His Pro Thr Thr Ile Ala Val Asp Val
                580                 585                 590

Ser Ala Pro Asp Gly Gln Leu Ile Val Glu Val Arg Asp Asp Gly Ile
                595                 600                 605

Gly Gly Ala Gln Pro Ser Gly Pro Gly Leu Arg Gly Ile Ala Asp Arg
610                 615                 620

Ala Glu Ala Phe Gly Gly Ser Leu Thr Val His Thr Asp Pro Gly Thr
625                 630                 635                 640

Gly Thr Thr Ile Arg Ala Leu Leu His Arg Ser Pro Leu Ser Ser
                645                 650                 655

Gly Arg Arg Ser Val Met Ile Glu Gly Cys Val Asp Val Ala Val
        660                 665                 670

Arg Arg Phe Arg Cys Arg Ser Arg Gly Ser Gly Ser Arg Arg Arg
        675                 680                 685

Arg Ser Ser Trp Arg Cys Gly Gly Ile Cys Gly Ser Arg Cys Arg Thr
690                 695                 700

Gly Met Ser Arg Ser Cys Ser Arg Asn Ala Ala Ser Lys Leu Ile Thr
705                 710                 715                 720

<210> SEQ ID NO 10
<211> LENGTH: 685
<212> TYPE: PRT
<213> ORGANISM: Rhodopseudomonas palent

<400> SEQUENCE: 10

Met Asp Ser Ile Leu Ala Pro Arg Ala Asp Ala Pro Arg Asn Ile Asp
1               5                   10                  15

Gly Ala Leu Arg Glu Ser Val Gln Gln Ala Ala Asp Trp Leu Val Ala
```

```
                    20                  25                  30
Asn Gln Lys Pro Asp Gly His Trp Val Gly Arg Ala Glu Thr Asn Ala
                35                  40                  45
Thr Met Glu Ala Gln Trp Cys Leu Ala Leu Trp Phe Leu Gly Leu Glu
            50                  55                  60
Asp His Pro Leu Arg Val Arg Leu Gly Arg Ala Leu Leu Asp Thr Gln
65                  70                  75                  80
Arg Pro Asp Gly Ala Trp His Val Phe Tyr Gly Ala Pro Asn Gly Asp
                85                  90                  95
Ile Asn Ala Thr Val Glu Ala Tyr Ala Ala Leu Arg Ser Leu Gly His
            100                 105                 110
Arg Asp Asp Glu Glu Pro Leu Arg Lys Ala Arg Asp Trp Ile Leu Ser
        115                 120                 125
Lys Gly Gly Leu Ala Asn Ile Arg Val Phe Thr Arg Tyr Trp Leu Ala
        130                 135                 140
Leu Ile Gly Glu Trp Pro Trp Glu Lys Thr Pro Asn Ile Leu Pro Glu
145                 150                 155                 160
Val Ile Trp Leu Pro Thr Trp Phe Pro Phe Ser Ile Tyr Asn Phe Ala
                165                 170                 175
Gln Trp Ala Arg Ala Thr Leu Met Pro Ile Ala Val Leu Ser Ala His
            180                 185                 190
Arg Pro Ser Arg Pro Leu Ala Pro Gln Asp Arg Leu Asp Ala Leu Phe
        195                 200                 205
Pro Gln Gly Arg Asp Ser Phe Asn Tyr Asp Leu Pro Ala Arg Leu Gly
        210                 215                 220
Ala Gly Val Trp Asp Val Ile Phe Arg Lys Ile Asp Thr Ile Leu His
225                 230                 235                 240
Arg Leu Gln Asp Trp Gly Ala Arg Arg Gly Pro His Gly Ile Met Arg
                245                 250                 255
Arg Gly Ala Ile Asp His Val Leu Gln Trp Ile Ile Arg His Gln Asp
            260                 265                 270
Tyr Asp Gly Ser Trp Gly Gly Ile Gln Pro Pro Trp Ile Tyr Gly Leu
        275                 280                 285
Met Ala Leu His Thr Glu Gly Tyr Ala Met Thr His Pro Val Met Ala
        290                 295                 300
Lys Ala Leu Asp Ala Leu Asn Glu Pro Gly Trp Arg Ile Asp Ile Gly
305                 310                 315                 320
Asp Ala Thr Phe Ile Gln Ala Thr Asn Ser Pro Val Trp Asp Thr Met
                325                 330                 335
Leu Ser Leu Leu Ala Phe Asp Asp Ala Gly Leu Gly Glu Arg Tyr Pro
            340                 345                 350
Glu Gln Val Glu Arg Ala Val Arg Trp Val Leu Lys Arg Gln Val Leu
        355                 360                 365
Val Pro Gly Asp Trp Ser Val Lys Leu Pro Asp Val Lys Pro Gly Gly
        370                 375                 380
Trp Ala Phe Glu Tyr Ala Asn Asn Phe Tyr Pro Asp Thr Asp Thr
385                 390                 395                 400
Ser Val Ala Leu Met Ala Leu Ala Pro Phe Arg His Asp Pro Lys Trp
                405                 410                 415
Gln Ala Glu Gly Ile Glu Asp Ala Ile Gln Arg Gly Ile Asp Trp Leu
            420                 425                 430
Val Ala Met Gln Cys Lys Glu Gly Gly Trp Gly Ala Phe Asp Lys Asp
        435                 440                 445
```

```
Asn Asp Lys Lys Ile Leu Ala Lys Ile Pro Phe Cys Asp Phe Gly Glu
            450                 455                 460

Ala Leu Asp Pro Pro Ser Ala Asp Val Thr Ala His Ile Ile Glu Ala
465                 470                 475                 480

Phe Ala Lys Val Gly Leu Asp Arg Asn His Pro Ser Ile Val Arg Ala
                485                 490                 495

Leu Asp Tyr Leu Lys Arg Glu Gln Glu Pro Glu Gly Pro Trp Phe Gly
            500                 505                 510

Arg Trp Gly Val Asn Tyr Val Tyr Gly Thr Gly Ala Val Leu Pro Ala
                515                 520                 525

Leu Ala Ala Ile Gly Glu Asp Met Arg Gln Pro Tyr Ile Ala Arg Ala
            530                 535                 540

Cys Asp Trp Leu Ile Ala Arg Gln Gln Ala Asn Gly Gly Trp Gly Glu
545                 550                 555                 560

Ser Cys Val Ser Tyr Met Asp Ala Lys Gln Ala Gly Glu Gly Thr Ala
                565                 570                 575

Thr Ala Ser Gln Thr Ala Trp Ala Leu Met Ala Leu Ile Ala Ala Asp
            580                 585                 590

Arg Pro Gln Asp Arg Asp Ala Ile Glu Arg Gly Cys Leu Tyr Leu Thr
            595                 600                 605

Glu Thr Gln Arg Asp Gly Thr Trp Gln Glu Val His Tyr Thr Gly Thr
610                 615                 620

Gly Phe Pro Gly Tyr Gly Val Gly Gln Thr Ile Lys Leu Asn Asp Pro
625                 630                 635                 640

Leu Leu Ser Lys Arg Leu Met Gln Gly Pro Glu Leu Ser Arg Ser Phe
                645                 650                 655

Met Leu Arg Tyr Asp Leu Tyr Arg His Tyr Phe Pro Met Met Ala Ile
            660                 665                 670

Gly Arg Val Leu Arg Gln Arg Gly Asp Arg Ser Gly His
            675                 680                 685

<210> SEQ ID NO 11
<211> LENGTH: 680
<212> TYPE: PRT
<213> ORGANISM: Streptomyces coelicolor

<400> SEQUENCE: 11

Met Thr Ala Thr Thr Asp Gly Ser Thr Gly Ala Ser Leu Arg Pro Leu
1               5                   10                  15

Ala Ala Ser Ala Ser Asp Thr Asp Ile Thr Ile Pro Ala Ala Ala Ala
                20                  25                  30

Gly Val Pro Glu Ala Ala Ala Arg Ala Thr Arg Arg Ala Thr Asp Phe
            35                  40                  45

Leu Leu Ala Lys Gln Asp Ala Glu Gly Trp Trp Lys Gly Asp Leu Glu
50                  55                  60

Thr Asn Val Thr Met Asp Ala Glu Asp Leu Leu Leu Arg Gln Phe Leu
65                  70                  75                  80

Gly Ile Gln Asp Glu Glu Thr Thr Arg Ala Ala Ala Leu Phe Ile Arg
                85                  90                  95

Gly Glu Gln Arg Glu Asp Gly Thr Trp Ala Thr Phe Tyr Gly Gly Pro
            100                 105                 110

Gly Glu Leu Ser Thr Thr Ile Glu Ala Tyr Val Ala Leu Arg Leu Ala
            115                 120                 125

Gly Asp Ser Pro Glu Ala Pro His Met Ala Arg Ala Ala Glu Trp Ile
            130                 135                 140
```

```
Arg Ser Arg Gly Gly Ile Ala Ser Ala Arg Val Phe Thr Arg Ile Trp
145                 150                 155                 160

Leu Ala Leu Phe Gly Trp Trp Lys Trp Asp Leu Pro Glu Leu Pro
                165                 170                 175

Pro Glu Leu Ile Tyr Phe Pro Thr Trp Val Pro Leu Asn Ile Tyr Asp
            180                 185                 190

Phe Gly Cys Trp Ala Arg Gln Thr Ile Val Pro Leu Thr Ile Val Ser
        195                 200                 205

Ala Lys Arg Pro Val Arg Pro Ala Pro Phe Pro Leu Asp Glu Leu His
210                 215                 220

Thr Asp Pro Ala Arg Pro Asn Pro Pro Arg Pro Leu Ala Pro Val Ala
225                 230                 235                 240

Ser Trp Asp Gly Ala Phe Gln Arg Ile Asp Lys Ala Leu His Ala Tyr
                245                 250                 255

Arg Lys Val Ala Pro Arg Arg Leu Arg Arg Ala Ala Met Asn Ser Ala
            260                 265                 270

Ala Arg Trp Ile Ile Glu Arg Gln Glu Asn Asp Gly Cys Trp Gly Gly
        275                 280                 285

Ile Gln Pro Pro Ala Val Tyr Ser Val Ile Ala Leu Tyr Leu Leu Gly
290                 295                 300

Tyr Asp Leu Glu His Pro Val Met Arg Ala Gly Leu Glu Ser Leu Asp
305                 310                 315                 320

Arg Phe Ala Val Trp Arg Glu Asp Gly Ala Arg Met Ile Glu Ala Cys
                325                 330                 335

Gln Ser Pro Val Trp Asp Thr Cys Leu Ala Thr Ile Ala Leu Ala Asp
            340                 345                 350

Ala Gly Val Pro Glu Asp His Pro Gln Leu Val Lys Ala Ser Asp Trp
        355                 360                 365

Met Leu Gly Glu Gln Ile Val Arg Pro Gly Asp Trp Ser Val Lys Arg
370                 375                 380

Pro Gly Leu Pro Pro Gly Gly Trp Ala Phe Glu Phe His Asn Asp Asn
385                 390                 395                 400

Tyr Pro Asp Ile Asp Asp Thr Ala Glu Val Val Leu Ala Leu Arg Arg
                405                 410                 415

Val Arg His His Asp Pro Glu Arg Val Glu Lys Ala Ile Gly Arg Gly
            420                 425                 430

Val Arg Trp Asn Leu Gly Met Gln Ser Lys Asn Gly Ala Trp Gly Ala
        435                 440                 445

Phe Asp Val Asp Asn Thr Ser Ala Phe Pro Asn Arg Leu Pro Phe Cys
450                 455                 460

Asp Phe Gly Glu Val Ile Asp Pro Pro Ser Ala Asp Val Thr Ala His
465                 470                 475                 480

Val Val Glu Met Leu Ala Val Glu Gly Leu Ala His Asp Pro Arg Thr
                485                 490                 495

Arg Arg Gly Ile Gln Trp Leu Leu Asp Ala Gln Glu Thr Asp Gly Ser
            500                 505                 510

Trp Phe Gly Arg Trp Gly Val Asn Tyr Val Tyr Gly Thr Gly Ser Val
        515                 520                 525

Ile Pro Ala Leu Thr Ala Ala Gly Leu Pro Thr Ser His Pro Ala Ile
530                 535                 540

Arg Arg Ala Val Arg Trp Leu Glu Ser Val Gln Asn Glu Asp Gly Gly
545                 550                 555                 560

Trp Gly Glu Asp Leu Arg Ser Tyr Arg Tyr Val Arg Glu Trp Ser Gly
                565                 570                 575
```

```
Arg Gly Ala Ser Thr Ala Ser Gln Thr Gly Trp Ala Leu Met Ala Leu
            580                 585                 590

Leu Ala Ala Gly Glu Arg Asp Ser Lys Ala Val Glu Arg Gly Val Ala
        595                 600                 605

Trp Leu Ala Ala Thr Gln Arg Glu Asp Gly Ser Trp Asp Glu Pro Tyr
    610                 615                 620

Phe Thr Gly Thr Gly Phe Pro Trp Asp Phe Ser Ile Asn Tyr Asn Leu
625                 630                 635                 640

Tyr Arg Gln Val Phe Pro Leu Thr Ala Leu Gly Arg Tyr Val His Gly
            645                 650                 655

Glu Pro Phe Ala Lys Lys Pro Arg Ala Ala Asp Ala Pro Ala Glu Ala
            660                 665                 670

Ala Pro Ala Glu Val Lys Gly Ser
        675                 680
```

BIOCATALYTIC PRODUCTION OF AMBROXAN

RELATED APPLICATIONS

This application is a national stage application (under 35 U.S.C. §371) of PCT/EP2010/057696, filed Jun. 2, 2010, which claims benefit of European application 09162104.5, filed Jun. 5, 2009.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing__13311__00081_US. The size of the text file is 63 KB, and the text file was created on Nov. 30, 2011.

The invention relates to the process for the biocatalytic production of ambroxan.

Compounds with the dodecahydronaphtho[2,1-b]furan skeleton are of great economic importance as aroma chemicals. Among these, compound 2 should be mentioned, (3aR, 5aS,9aS,9bR)-3a,6,6,9a-tetramethyldodecahydro-naphtho-[2,1-b]-furan), known as the levorotatory stereoisomer [(−)-2] of ambroxan.

Originally obtained from sperm whales' ambergris, there are currently predominantly two routes via which ambroxan can be obtained. Sclareol (3), a constituent of clary sage (*Salvia sclarea*), is frequently used as a starting material for semisynthetic material because it already comprises the optical information for the compound ((−)-2). Here, the oxidative degradation can be carried out using chromic acid, permanganate, $H_2O_2$ or ozone [Stoll et al.; Helv. Chim. Acta (1950), 33: 1251]. The resulting sclareolid (4) is subsequently reduced (for example using $LiAlH_4$ or $NaBH_4$) to give ambrox-1,4-diol (5) [Mookherjee et al.; Perfumer and Flavourist (1990), 15: 27]. Compound (4) can also be prepared from sclareol (3) by means of a biotransformation using *Hyphozyma roseoniger* [EP 204009].

Finally, ambrox-1,4-diol (5) can be cyclized in a series of chemical processes to give compound ((−)-2). The preparation of the racemate of ambroxan, rac-2, has been accomplished, inter alia, via homofarnesylic acid [U.S. Pat. No. 513,270; Lucius et al.; Chem. Ber. (1960), 93: 2663] and 4-(2,6,6-trimethylcyclohex-1-enyl)butan-2-one [Büchi et al.; Helv. Chim. Acta (1989), 72: 996]. Ambroxan's market volume in 2002 was currently 20 tonnes per year on average. This requires approximately 33 tonnes of sclareol per year as starting material. 207 tonnes of various individual substances are required to produce one tonne of ambroxan, and these, in turn, generate 206 tonnes of waste. The substances generated have different, but in total relatively potent, effects on health and environment [Deutsche Bundesstiftung Umwelt (German Federal Foundation for the Environment)]. Thus, this synthesis requires a high input of energy and the use of polluting chemicals.

The biocatalytic synthesis of compound ((−)-2) has been described in the literature [Neumann et al.; Biol. Chem. Hoppe Seyler (1986), 367: 723]. Here, the molecule is obtained from homofarnesol (compound (1), (3Z,7E)-4,8,12-trimethyltrideca-3,7,11-trien-1-ol). The catalyst used was squalene-hopene cyclase (SHC) from *Alicyclobacillus acidocaldarius* (formerly *Bacillus acidocaldarius*). The enzyme naturally catalyzes the cyclization of squalene to hopane. By way of secondary reaction, this SHC is obviously also capable of reacting compound (1) to give ambroxan ((−)-2). The biocatalyst can be produced by recombinant means [Ochs D. et al.; J. Bacteriol. (1992), 174: 298]. According to Neumann et al., however, the rate at which the cyclization of homofarnesol to ambroxan proceeds is merely 1.2% (calculated on the basis of the GC peaks), and the specific activity regarding the cyclization of homofarnesol is given as 0.02 mU/mg protein.

The object of the present invention was therefore to provide a novel process for the production of ambroxan and derivatives thereof which have advantages over the technically complex prior-art syntheses. By employing biotechnological processes, it was intended to avoid the generation of pollut-

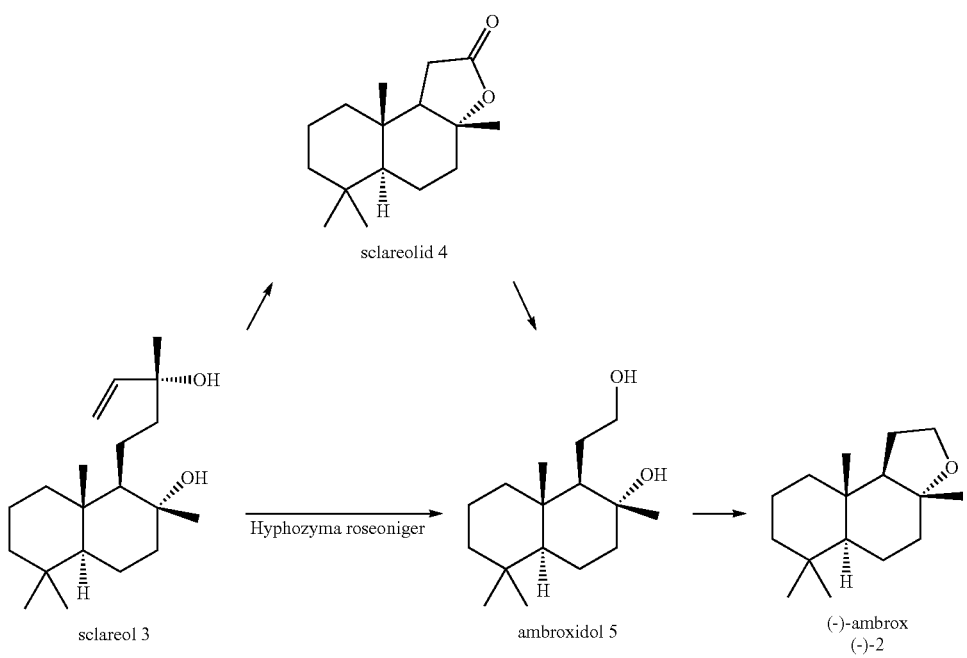

ants and drastically to reduce the expenditure of energy. A further object was additionally to reduce the costs incurred, by using readily available starting materials and by reducing the number of chemical reactions (or steps). Furthermore, it was intended to achieve a high productivity.

This object is achieved by a process for the preparation of ambroxan derivatives, preferably ambroxan, of the general formula (2), characterized in that homofarnesol derivatives of the general formula (1) are converted biocatalytically into the corresponding ambroxan derivatives by means of a polypeptide with the activity of a homofarnesol-ambroxan cyclase by way of enzyme.

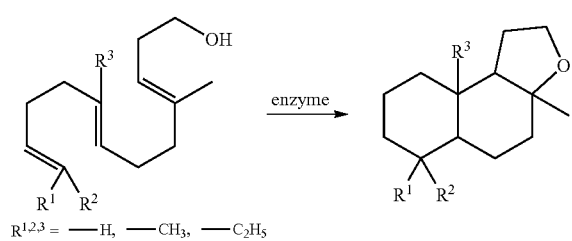

$R^{1,2,3}$ = ——H, ——$CH_3$, ——$C_2H_5$

Derivatives are in particular stereoisomers, preferably enantiomers, but also diastereomers, of the compound (2). In one embodiment of the present invention, derivatives of homofarnesol, or ambroxan, are substituted compounds (1) and (2), where the substituents are inert towards the biocatalyzed reaction. This means in particular compounds of the structural formulae shown hereinbelow.

For the purposes of the invention, the terms "compound (1), "homofarnesol", "4,8,12-trimethyltrideca-3,7,11-trien-1-ol)" and derivatives of homofarnesol, and the terms "compound (2)", "ambroxan", "dodecahydronaphtho[2,1-b]furan" and derivatives of ambroxan are synonyms and mutually exchangeable and replaceable, unless expressly defined otherwise.

In a preferred variant of the invention, the reaction product is the levorotatory ambroxan of the formula ((−)-2):

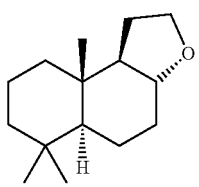

(−)-ambroxan 2

Polypeptides with the activity of a homofarnesol-ambroxan cyclase are a novel class of enzymes.

The term "activity" describes the ability of an enzyme to react a substrate to give a product. The activity can be determined in what is known as an activity test via the increase of the product, the decrease of the substrate (or starting materials), or via a combination of these parameters as a function of time.

The enzymes according to the invention are characterized in that their activity is the reaction of homofarnesol into ambroxan.

For the purposes of the invention, the main substrate in one variant is the chemical compound which, in comparison with all other compounds which are capable of being converted by the enzyme, amounts to the most important reactant of homofarnesol-ambroxan cyclase, expressed in mol percent.

For the purposes of the invention, the main substrate in one variant is homofarnesol, and thus the main activity, and thus the main reaction of a homofarnesol-ambroxan cyclase is the reaction with the main substrate homofarnesol.

The activity of the homofarnesol-ambroxan cyclase is, in one variant of the invention, defined via the yield in mol percent. Preferably, the reaction of homofarnesol into ambroxan in the presence of an enzyme of the novel class of the homofarnesol-ambroxan cyclases generates an ambroxan yield of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, given in mol percent and based on the mols of homofarnesol employed; especially preferably, the yield is between 5 and 100, 10 and 100, and 100, 25 and 100, 30 and 100, 35 and 100, in particular between 40 and 100, 45 and 100, 50 and 100, 60 and 100, 70 and 100 mol percent.

In a further variant of the invention, the activity of the homofarnesol-ambroxan cyclase is defined via the reaction rate (amount of product/(amount of product+amount of remaining starting material)*100) in mol percent. Preferably, the reaction of homofarnesol into ambroxan in the presence of an enzyme of the novel class of the homofarnesol-ambroxan cyclases generates an ambroxan yield of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, given in mol percent and based on the mols of homofarnesol employed; especially preferably, the yield is between 5 and 100, 10 and 100, 20 and 100, 25 and 100, 30 and 100, 35 and 100, in particular between 40 and 100, 45 and 100, 50 and 100, 60 and 100, 70 and 100.

In a preferred embodiment of the invention, the yield and/or the reaction rate are determined over a defined period of time of, for example, 4, 6, 8, 10, 12, 16, 20, 24, 36 or 48 hours, during which homofarnesol is converted into ambroxan by the cyclases according to the invention. In a further variant, the reaction is carried out under precisely defined conditions of, for example, 25, 30, 40, 50 or 60° C. In particular, the yield and/or the reaction rate are determined by carrying out the reaction of converting homofarnesol into ambroxan by the cyclases according to the invention at 30° C. over 16 hours.

In one embodiment of the invention, a 10 mM homofarnesol solution (citrate-buffer) is reacted with a cyclase solution in order to determine the yield and/or the reaction rate, the enzyme being present in the form of a membrane protein extract of homofarnesol-ambroxan-cyclases-extracting cells (isolated as described in [Ochs D. et al.; J. Bacteriol. (1992), 174: 298]) at a concentration of 0.08% by weight protein content.

In a further embodiment of the present invention, a homofarnesol-ambroxan cyclase is characterized in that it shows a 2-, 3-, 4-, 5-, 6-, 7-, 8-, 9-, 10-, 11-, 12-, 13-, 14-, 15-, 16-, 17-, 18-, 19-, 20-, 21-, 22-, 23-, 24-, 25-, 26-, 27-, 28-, 29-, 30-, 31-, 32-, 33-, 34-, 35-, 36-, 37-, 38-, 39-, 40-, 41-, 42-, 43-, 44-, 45-, 46-, 47-, 48-, 49-, 50-, 51-, 52-, 53-, 54-, 55-, 56-, 57-, 58-, 59-, 60-, 61-, 62-, 63-, 64-, 65-, 66-, 67-, 68-, 69-, 70-, 71-, 72-, 73-, 74-, 75-, 76-, 77-, 78-, 79-, 80-, 81-, 82-, 83-, 84-, 85-, 86-, 87-, 88-, 89-, 90-, 91-, 92-, 93-, 94-, 95-, 96-, 97-, 98-, 99-, 100-, 200-, 500-, 1000-fold or higher yield and/or reaction rates in the reaction of homofarnesol to give ambroxan in comparison with the squalene-hopene cyclase (SHC) from *Alicyclobacillus acidocaldarius* (formerly *Bacillus acidocaldarius*) on the same conditions. Here, the term condition relates to reaction conditions such as substrate concentration, enzyme concentration, reaction period and/or temperature.

In one variant of the present invention, a homofarnesol-ambroxan cyclase is characterized by each or by a plurality of the abovementioned definitions, in any desired combination.

The invention also relates to a process for the production of ambroxan in which
a) homofarnesol is brought into contact and/or incubated with homofarnesol-ambroxan cyclase,
b) ambroxan is isolated.

In one embodiment of the invention, homofarnesol is brought into contact and/or incubated with homofarnesol-ambroxan cyclase in a medium such that homofarnesol is converted into ambroxan in the presence of the cyclase. The medium is preferably an aqueous reaction medium. The aqueous reaction media are preferably buffered solutions which, as a rule, have a pH of preferably from 5 to 8. The buffer used may be a citrate, phosphate, TRIS (tris(hydroxymethyl)aminomethane), MES (2-(N-morpholino)ethanesulfonic acid) buffer. Furthermore, the reaction medium may comprise other additives such as, for example, detergents (for example taurodeoxycholate).

The substrate (1) is preferably employed in the enzymatic reaction at a concentration of 5-100 mM, especially preferably 15-25 mM, and can be fed in continuously or batchwise.

As a rule, the enzymatic cyclization reaction takes place at the reaction temperature of below the deactivation temperature of the cyclase employed and above −10° C. Especially preferably, it is in the range of from 0 to 100° C., in particular from 15 to 60° C. and specifically from 20 to 40° C., for example at approximately 30° C.

The reaction product ambroxan can be extracted using organic solvents, selected from the group of those mentioned hereinbelow, and optionally distilled for purification purposes.

In a further variant of the invention, two-phase systems are also employed besides these single-phase aqueous systems. Here, ionic liquids are used as the second phase, but preferably organic reaction media which are not miscible with water are used as the second phase. Thereby, the reaction products accumulate in the organic phase. After the reaction, ambroxan in the organic phase can be separated readily from the aqueous phase, which comprises the biocatalyst.

Nonaqueous reaction media are understood as meaning reaction media which comprise less than 1% by weight, preferably less than 0.5% by weight, of water, based on the total weight of the liquid reaction medium. In particular, the reaction can be carried out in an organic solvent.

Examples of suitable organic solvents are, for example, aliphatic hydrocarbons, preferably those having 5 to 8 carbon atoms, such as pentane, cyclopentane, hexane, cyclohexane, heptane, octane or cyclooctane, halogenated aliphatic hydrocarbons, preferably those having one or two carbon atoms, such as dichloromethane, chloroform, carbon tetrachloride, dichloroethane or tetrachloroethane, aromatic hydrocarbons, such as benzene, toluene, the xylenes, chlorobenzene or dichlorobenzene, aliphatic acyclic and cyclic ethers or alcohols, preferably those having 4 to 8 carbon atoms, such as ethanol, isopropanol, diethyl ether, methyl tert.-butyl ether, ethyl tert.-butyl ether, dipropyl ether, diisopropyl ether, dibutyl ether, tetrahydrofuran or esters such as ethyl acetate or n-butyl acetate or ketones such as methyl isobutyl ketone or dioxane or mixtures of these. The solvents which are especially preferably used are the abovementioned heptane, methyl tert.-butyl ether, diisopropyl ether, tetrahydrofuran, ethyl acetate.

In one embodiment of the present invention, the starting material employed for the synthesis of ambroxan is citral. This is a particular advantage of the process according to the invention since citral is inexpensive and available in large quantities. In a classical synthesis, citral is reacted to give homofarnesol

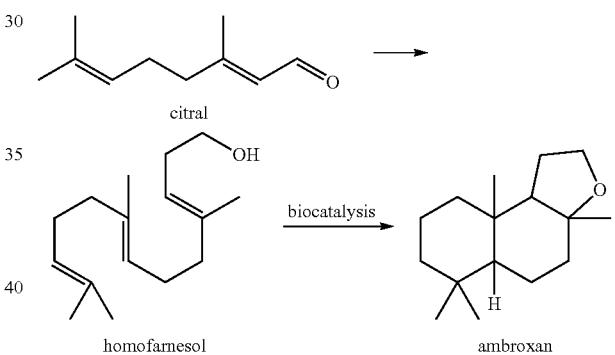

In one embodiment of the present invention, the reaction of citral into homofarnesol is carried out via the following steps (for example: JOC, (1992), 57, 2794):

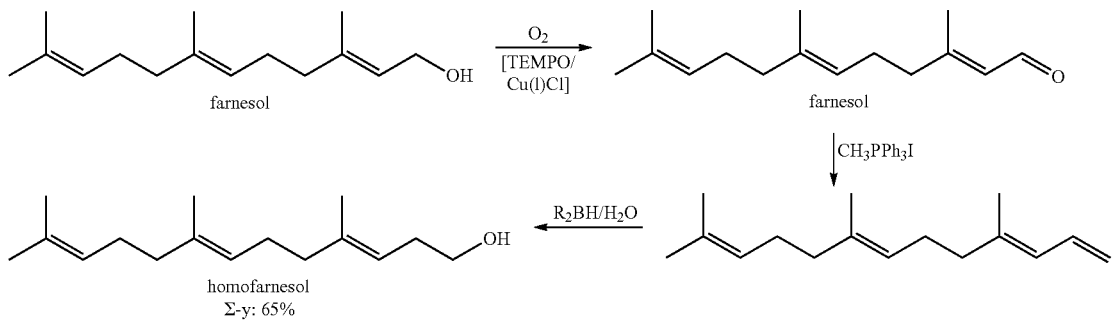

Thereby, the process according to the invention has the further advantage that the entire reaction of homofarnesol to give ambroxan takes place in single-phase aqueous systems, but also in two-phase systems.

In the case of the two-phase systems, those mentioned above are employed. It is preferred to use the abovementioned organic solvents which are not miscible with water as the second phase. Thereby, the reaction product will accumulate in the organic phase. After the reaction, ambroxan in the organic phase can be separated readily from the aqueous phase which contains the biocatalyst.

When carrying out the invention with citral as the starting material, too, homofarnesol is brought into contact and/or incubated with homofarnesol-ambroxan cyclase in a medium in such a way that homofarnesol is reacted to give ambroxan in the presence of the cyclase. The medium is preferably an aqueous reaction medium. The aqueous reaction media are preferably buffer solutions which, as a rule, have a pH of preferably 5 to 8. The buffer used may be a citrate, phosphate, TRIS (tris(hydroxymethyl)aminomethane), MES (2-(N-morpholino)ethanesulfonic acid) buffer. The reaction medium may furthermore comprise other additives such as, for example, detergents (taurodeoxycholate or similar).

In one embodiment of the invention, the reaction product ambroxan will be extracted with organic solvent selected from the group of those mentioned hereinbelow and optionally distilled for purification purposes.

A further subject matter of the present invention is a process for the biocatalytic production of ambroxan, wherein the enzyme is a polypeptide which is encoded by a nucleic acid molecule comprising at least one nucleic acid molecule selected from the group consisting of:
a) nucleic acid molecule which codes for a polypeptide comprising the in SEQ ID NO 2, 5, 6, 7, 8, 9, 10 or 11;
b) nucleic acid molecule which comprises at least one polynucleotide of the sequence shown in SEQ ID NO 1;
c) nucleic acid molecule which codes for a polypeptide whose sequence has an identity of at least 46% to the sequences SEQ ID NO 2, 5, 6, 7, 8, 9, 10 or 11;
d) nucleic acid molecule according to (a) to (c), which for a functionally equivalent polypeptide or a fragment of the sequence according to SEQ ID NO 2, 5, 6, 7, 8, 9, 10 or 11;
e) nucleic acid molecule, coding for a functionally equivalent polypeptide with the activity of a homofarnesol-ambroxan cyclase, which is obtained by amplifying a nucleic acid molecule from a cDNA library or from genomic DNA using the primers according to sequence nos. 3 and 4, or by chemically synthesizing the nucleic acid molecule by de novo synthesis;
f) nucleic acid molecule, coding for a functionally equivalent polypeptide with the activity of a homofarnesol-ambroxan cyclase which hybridizes with a nucleic acid molecule according to (a) to (c) under stringent conditions;
g) nucleic acid molecule, coding for a functionally equivalent polypeptide with the activity of a homofarnesol-ambroxan cyclase, which can be isolated from a DNA library using a nucleic acid molecule according to (a) to (c) or their partial fragments of at least 15 nt, preferably 20 nt, 30 nt, 50 nt, 100 nt, 200 nt or 500 nt by way of probe under stringent hybridization conditions; and
h) nucleic acid molecule, coding for a functionally equivalent polypeptide with the activity of a homofarnesol-ambroxan cyclase, where the sequence of the polypeptide has an identity of at least 46% to the sequences SEQ ID NO 2, 5, 6, 7, 8, 9, 10 or 11;
i) nucleic acid molecule, coding for a functionally equivalent polypeptide with the activity of a homofarnesol-ambroxan cyclase, where the polypeptide is encoded by a nucleic acid molecule selected from the group of those described in a) to h) and has been isolated, or can be isolated, by means of a monoclonal antibody,
j) nucleic acid molecule, coding for a functionally equivalent polypeptide with the activity of a homofarnesol-ambroxan cyclase, where the polypeptide has an analogous or similar binding site as a polypeptide encoded by a nucleic acid molecule selected from the group of those described in a) to h).

For the purposes of the invention, analogous or similar binding site is a conserved domain or motif of the amino acid sequence with a homology of 80%, especially preferably 85%, 86%, 87%, 88%, 89%, 90%, in particular 91%, 92%, 93%, 94%, 95%, 96%, 97%, 98% or 99% or 100%, which ensures the binding of the same substrate, in particular homofarnesol.

Preferably, the nucleic acid molecule c) has an identity to SEQ ID NO: 1 of at least 46%, 47%, 48%, 49%, 50%, 55%, 60%, 65%, 70%, 75%, 80%, especially preferably 85%, 86%, 87%, 88%, 89%, 90%, in particular 91%, 92%, 93%, 94%, 95%, 96%, 97%, 98% or 99%.

Likewise, a functionally equivalent polypeptide has an identity to SEQ ID NO: 2 of at least 46%, 47%, 48%, 49%, 50%, 55%, 60%, 65%, 70%, 75%, 80%, especially preferably 85%, 86%, 87%, 88%, 89%, 90%, in particular 91%, 92%, 93%, 94%, 95%, 96%, 97%, 98% or 99%.

Instead of the term "identity", it is also possible to use the term "homologous" or "homology" as equivalent.

The identity between two nucleic acid sequences or polypeptide sequences is calculated by comparison with the aid of the program Bestfit based on the algorithm of Smith, T. F. and Waterman, M. S. (Adv. Appl. Math. 2: 482-489 (1981)).

Preferably, the identity between two nucleic acid sequences or polypeptide sequences is defined via the identity of the nucleic acid sequence/polypeptide sequence over the in each case entire sequence length, as it is calculated by comparison with the aid of the program GAP based on the algorithm of Needleman, S. B. and Wunsch, C. D. (J. Mol. Biol. 48: 443-453)).

It is preferred to carry out the identity comparisons by setting the following parameters for amino acids:
Gap creation penalty: 8; Gap extension penalty: 2
and the following parameters for nucleic acids:
Gap creation penalty: 50; Gap extension penalty: 3.

One embodiment of the invention proposes the identity between two nucleic acid sequences or polypeptide sequences by comparison with the aid of the program BLASTP 2.2.20+ with standard settings as proposed pursuant to NCBI Blast (Reference: Altschul et al., (1997), Nucleic Acids Res. 25:3389-3402. Reference for compositional score matrix adjustment: Altschul et al., (2005), FEBS J. 272:5101-5109.)

Subject matter of the invention are further homologues or functional equivalents of SEQ ID NO: 1 which hybridize with this nucleic acid sequence under stringent conditions.

In this context, "functional equivalents" describe, in principle, nucleic acid sequences which hybridize under standard conditions with a nucleic acid sequence or parts of a nucleic acid sequence and which are capable of bringing about the expression of a protein with the same properties as those of homofarnesol-ambroxan cyclase in a cell or an organism.

To carry out the hybridization, it is advantageous to employ short oligonucleotides with a length of approximately 10-50 bp, preferably 15-40 bp, for example of the conserved or other regions, which can be determined in a manner with which the skilled worker is familiar by comparison with other related genes. However, it is also possible to employ longer fragments of the nucleic acids according to the invention with a length of 100-500 bp or the complete sequences for the hybridization. Depending on the nucleic acid/oligonucleotide used, the length of the fragment or the entire sequence, or depending on which type of nucleic acid, i.e. DNA or RNA, is used for the hybridization, these standard conditions vary. Thus, for example, the melting points for DNA:DNA hybrids are approximately 10° C. lower than those of DNA:RNA hybrids of the same length.

Standard hybridization conditions are to be understood, for example, as meaning temperatures of between 42 and 58° C. in an aqueous buffer solution with a concentration of between 0.1 to 5×SSC (1×SSC=0.15 M NaCl, 15 mM sodium citrate, pH 7.2) or additionally in the presence of 50% formamide such as, for example, 42° C. in 5×SSC, 50% formamide, depending on the nucleic acid. The hybridization conditions for DNA-DNA hybrids are advantageously 0.1×SSC and temperatures of between approximately 20° C. to 65° C., preferably between approximately 30° C. to 45° C. For DNA:RNA hybrids, the hybridization conditions are advantageously 0.1×SSC and temperatures of between approximately 30° C. to 65° C., preferably between approximately 45° C. to 55° C. These temperatures which have been stated for the hybridization are melting points which have been calculated by way of example for a nucleic acid with a length of approximately 100 nucleotides and a G+C content of 50% in the absence of formamide. The experimental conditions for the DNA hybridization are described in relevant textbooks of genetics, such as, for example, Sambrook et al., "Molecular Cloning", Cold Spring Harbor Laboratory, 1989, and can be calculated using formulae known to the skilled worker, for example as a function of the length of the nucleic acids, the nature of the hybrid or the G+C content. Further information on hybridization can be found by the skilled worker in the following textbooks: Ausubel et al. (eds.), 1985, "Current Protocols in Molecular Biology", John Wiley & Sons, New York; Hames and Higgins (eds.), 1985, "Nucleic Acids Hybridization: A Practical Approach", IRL Press at Oxford University Press, Oxford; Brown (ed.), 1991, Essential Molecular Biology: A Practical Approach, IRL Press at Oxford University Press, Oxford.

A functional equivalent is furthermore also understood as meaning nucleic acid sequences which are homologous, or identical, to a certain nucleic acid sequence ("original nucleic acid sequence") up to a defined percentage and which demonstrate the same activity as the original nucleic acid sequences, furthermore in particular also natural or artificial mutations of these nucleic acid sequences.

"Functional equivalents" or analogues of the specifically disclosed enzymes are, for the purpose of the present invention, polypeptides which differ from the former and which furthermore demonstrate the desired biological activity, such as, for example, main activity, substrate specificity. Thus, for example, "functional equivalents" are understood as meaning enzymes which catalyze the model reaction and which have at least 20%, 30%, 50%, 60%, 65%, 70%, 75%, 80%, especially preferably 85%, 86%, 87%, 88%, 89%, 90%, in particular 91%, 92%, 93%, 94%, 95%, 96%, 97%, 98%, or 99% of the activity of an enzyme comprising one of the amino acid sequences specified under SEQ ID NO: 2, 5, 6, 7, 8, 9, 10 or 11.

"Functional equivalents" are, in accordance with the invention, in particular also understood as meaning mutants which have an amino acid which is not the specifically mentioned amino acid in at least one sequence position of the abovementioned amino acid sequences while retaining one of the abovementioned biological activities. Thus, "functional equivalents" encompass the mutants obtainable by one or more amino acid additions, substitutions, deletions and/or inversions, it being possible for the abovementioned modifications to occur in any sequence position as long as they lead to a mutant with the property profile according to the invention. In particular, functional equivalents also exist when the reactivity patterns between mutant and unmodified polypeptide agree in terms of quality, i.e. for example when identical substrates are converted at different rates.

Examples of suitable amino acid substitutions can be seen from the table which follows:

| Original residue | Examples of the substitution |
| --- | --- |
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

"Functional equivalents" in the above sense are also "precursors" of the polypeptides described, and "functional derivatives".

In this context, "precursors" are natural or synthetic precursors of the polypeptide with or without the desired biological activity.

"Functional derivatives" of polypeptides according to the invention can likewise be prepared as functional amino acid side groups or at their N- or C-terminal end, using known techniques. Such derivatives comprise, for example, aliphatic esters of carboxylic acid groups, amides of carboxylic acid groups, obtainable by reaction with ammonia or with a primary or secondary amide; N-acyl derivatives of free amino groups, prepared by reactions of acyl groups; or O-acyl derivatives of free hydroxyl groups, prepared by reaction with acyl groups.

In the event of a possible protein glycosylation, "functional equivalents" according to the invention comprise proteins of the above-described type in deglycosylated or glycosylated form, and modified forms obtainable by modifying the glycosylation pattern.

"Functional equivalents" naturally also comprise polypeptides which can be obtained from other organisms, and naturally occurring variants. For example, sequence comparison allows regions of homologous sequence regions to be determined and equivalent enzymes to be found on the basis of the specific guidelines of the invention.

"Functional equivalents" likewise comprise fragments, preferably individual domains or sequence motifs, of the polypeptides of the invention, which fragments have, for example, the desired biological function.

"Functional equivalents" are, moreover, fusion proteins which comprise any of the abovementioned polypeptide sequences or functional equivalents derived therefrom and at least one further heterologous sequence which is functionally different therefrom and is functionally N-terminally or C-terminally linked (i.e. without any substantial reciprocal functional impairment of the fusion protein moiety). Nonlimiting examples of such heterologous sequences are, for example, signal peptides or enzymes.

Homologues of the proteins according to the invention can be identified by screening combinatorial libraries of mutants such as truncation mutants, for example. For example, a variegated library of protein variants may be generated by combinatorial mutagenesis at the nucleic acid level, for example by enzymatically ligating a mixture of synthetic oligonucleotides. There exist a large number of processes which may be used for the preparation of libraries of potential homologues from a degenerate oligonucleotide sequence. A degenerate gene sequence may be synthesized chemically in a DNA synthesizer, and the synthetic gene may then be ligated into a suitable expression vector. Using a degenerate set of genes makes it possible to prepare all the sequences in a mixture which encode the desired set of potential protein sequences. Processes for synthesizing degenerate oligonucleotides are known to a person skilled in the art (e.g. Narang, S. A. (1983) Tetrahedron 39:3; Itakura et al. (1984) Annu. Rev. Biochem. 53:323; Itakura et al., (1984) Science 198:1056; Ike et al. (1983) Nucleic Acids Res. 11:477).

A plurality of techniques for screening gene products of combinatorial libraries which have been prepared by point mutations or truncations and for screening cDNA libraries for gene products having a selected property are known from the prior art. These techniques can be adapted for rapidly screening the gene libraries which have been generated by combinatorial mutagenesis of homologues according to the invention. The most frequently employed techniques for screening large gene libraries which are subject to high-throughput analysis comprise cloning the gene library into replicable expression vectors, transforming the appropriate cells with the resulting vector library, and expressing the combinatorial genes under conditions under which detection of the desired activity facilitate the isolation of the vector which encodes the gene whose product was detected. Recursive ensemble mutagenesis (REM), a technique which increases the frequency of functional mutants in the libraries, may be used in combination with the screening tests in order to identify homologues (Arkin and Yourvan (1992) PNAS 89:7811-7815; Delgrave et al. (1993) Protein Engineering 6(3):327-331).

Subject matter of the invention are furthermore nucleic acid sequences (single- and double-stranded DNA and RNA sequences such as, for example, cDNA and mRNA) which code for an enzyme with cyclase activity according to the invention. Preferred are nucleic acid sequences which code for example for amino acid sequences according to SEQ ID NO: 2, 5, 6, 7, 8, 9, 10 or 11 or characteristic partial sequences thereof.

All of the nucleic acid sequences mentioned herein can be prepared in a manner known per se by means of chemical synthesis starting from the nucleotide building blocks, such as, for example, by means of fragment condensation of individual overlapping, complementary nucleic acid building blocks of the double helix. Oligonucleotides may, for example, be synthesized chemically, in a known manner, using the phosphoamidite method (Voet, Voet, $2^{nd}$ edition, Wiley Press New York, pages 896-897). The assembly of synthetic oligonucleotides and the filling-in of gaps with the aid of the DNA polymerase Klenow fragment and ligation reactions and also general cloning methods are described by Sambrook et al. (1989), Molecular Cloning: A laboratory manual, Cold Spring Harbor Laboratory Press.

Further embodiments for carrying out the biocatalytic process according to the invention for the production of ambroxan:

The process according to the invention comprises that the enzyme is present in a form selected from the group consisting of:
a) free, optionally purified or partially purified polypeptide with the activity of a homofarnesol-ambroxan cyclase;
b) immobilized polypeptide with the activity of a homofarnesol-ambroxan cyclase;
c) polypeptide, isolated from cells, according to a) or b);
d) intact cell, optionally quiescent or disrupted cells, comprising at least one polypeptide with the activity of a homofarnesol-ambroxan cyclase;
e) cell lysate or cell homogenate of the cells described under d).

In one embodiment of the invention, the cells are microorganisms, preferably transgenic microorganisms, expressing at least one heterologous nucleic acid molecule coding for a polypeptide with the activity of a homofarnesol-ambroxan cyclase.

Further subject matter of the present invention are therefore also a gene construct or a vector comprising a nucleic acid molecule coding for a polypeptide with the activity of a homofarnesol-ambroxan cyclase, preferably a nucleic acid molecule comprising at least one nucleic acid molecule selected from the group consisting of:
a) nucleic acid molecule which codes for a polypeptide comprising the in SEQ ID NO 2, 5, 6, 7, 8, 9, 10 or 11;
b) nucleic acid molecule which comprises at least one polynucleotide of the sequence shown in SEQ ID NO 1;
c) nucleic acid molecule which codes for a polypeptide whose sequence has an identity of at least 46% to the sequences SEQ ID NO 2, 5, 6, 7, 8, 9, 10 or 11;
d) nucleic acid molecule according to (a) to (c), which for a fragment of the sequence according to SEQ ID NO 2, 5, 6, 7, 8, 9, 10 or 11;
e) nucleic acid molecule, coding for a functionally equivalent polypeptide with the activity of a homofarnesol-ambroxan cyclase, which is obtained by amplifying a nucleic acid molecule from a cDNA library or from a genomic library using the primers according to sequence nos. 3 and 4;
f) nucleic acid molecule, coding for a polypeptide with the activity of a homofarnesol-ambroxan cyclase which hybridizes with a nucleic acid molecule according to (a) to (c) under stringent conditions;
g) nucleic acid molecule, coding for a polypeptide with the activity of a homofarnesol-ambroxan cyclase, which can be isolated from a DNA library using a nucleic acid molecule according to (a) to (c) or their partial fragments of at least 15 nt, preferably 20 nt, 30 nt, 50 nt, 100 nt, 200 nt or 500 nt by way of probe under stringent hybridization conditions; and
h) nucleic acid molecule, coding for a polypeptide with the activity of a homofarnesol-ambroxan cyclase, where the sequence of the polypeptide has an identity of at least 46% to the sequences SEQ ID NO 2, 5, 6, 7, 8, 9, 10 or 11;
i) nucleic acid molecule, coding for a functionally equivalent polypeptide with the activity of a homofarnesol-ambroxan cyclase, where the polypeptide is encoded by a nucleic acid molecule selected from the group of those described in a) to h) and has been isolated, or can be isolated, by means of a monoclonal antibody,
j) nucleic acid molecule, coding for a functionally equivalent polypeptide with the activity of a homofarnesol-ambroxan cyclase, where the polypeptide has an analogous or similar binding site as a polypeptide encoded by a nucleic acid molecule selected from the group of those described in a) to h).

Furthermore, the host cells comprising a gene construct or a vector as described hereinabove are likewise subject matter of the present invention. To this end, the nucleic acid sequences used are advantageously introduced into a transgenic gene construct which can ensure the transgenic expression of a homofarnesol-ambroxan cyclase in an organism, preferably a microorganism.

In the gene construct, a nucleic acid molecule coding for a homofarnesol-ambroxan cyclase will, in this context, preferably be functionally linked to at least one genetic control element (for example a promoter and/or terminator) which ensures the expression in an organism, preferably a microorganism.

A functional linkage is understood as meaning, for example, the sequential arrangement of a promoter with the nucleic acid sequence to be expressed, which codes for a homofarnesol-ambroxan cyclase (for example the sequence according to SEQ ID NO: 1) and optionally further regulatory elements such as, for example, a terminator in such a way that each of the regulatory elements is capable of carrying out its function upon transgenic expression of the nucleic acid sequence. A direct linkage in the chemical sense is not necessarily required for this purpose. Generating a functional linkage, and the preparation of the gene construct, can be performed by means of customary recombination and cloning techniques as are described, for example, in Maniatis T, Fritsch E F and Sambrook J (1989) Molecular Cloning: A Laboratory Manual, Cold Spring Harbor Laboratory, Cold Spring Harbor (NY), in Silhavy T J, Berman M L and Enquist L W (1984) Experiments with Gene Fusions, Cold Spring Harbor Laboratory, Cold Spring Harbor (NY), in Ausubel F M et al. (1987). However, other sequences which, for example, act as a linker with specific restriction enzyme cleavage sites or as a signal peptide, may also be positioned between the two sequences. Also, the inversion sequences may lead to the expression of fusion proteins. Preferably, the gene construct consisting of a linkage of promoter and nucleic acid sequence to be expressed can be present in integrated form in a vector, and can be inverted into a microorganism for example by transformation.

The nucleic acid sequences present in the gene constructs or vectors can be linked functionally not only to a promoter, but also to further genetic control sequences. The term "genetic control sequences" is to be understood broadly and refers to all those sequences which have an effect on the generation or the function of the gene construct. For example, genetic control sequences modify transcription and translation in prokaryotic or eukaryotic organisms. Preferably, the gene constructs comprise control sequence and optionally further customary regulatory elements, in each case in functional linkage with the nucleic acid sequence to be expressed transgenically.

Control sequences are understood as being those which make possible the homologous recombination or inversion into the genome of a host organism, or which permit removal from the genome. In the case of homologous recombination, for example, the coding sequence of a certain endogenous gene can be exchanged for a dsRNA-encoding sequence in targeted manner.

A gene construct and the vectors derived therefrom may comprise further functional elements. The term "functional element" is to be understood in the broad sense and refers to all those elements which have an effect on the generation, multiplication or function of the expression cassettes, vectors or transgenic organisms according to the invention. The following may be mentioned by way of example, but not by way of limitation:

a) selection markers which confer resistance to antiobiotics or biocides, such as, for example, kanamycin, G 418, bleomycin, hygromycin and the like.

b) reporter genes which code for readily quantifiable proteins and which, via intrinsic color or enzymatic activity, ensure that the transformation efficiency or the location or time of expression can be assessed. Very especially preferred in this context are reporter proteins (Schenborn E, Groskreutz D. Mol. Biotechnol. 1999; 13(1):29-44) such as the "green fluorescence protein" (GFP) (Scheen et al. (1995) Plant Journal 8(5):777-784), chloramphenicol transferase, a luciferase (Ow et al. (1986) Science 234:856-859), the aequorin gene (Prasher et al. (1985) Biochem. Biophys. Res. Commun. 126 (3):1259-1268), beta-galactosidase, with particular preference for β-glucuronidase (Jefferson et al. (1987) EMBO J. 6:3901-3907).

c) Replication origins which ensure the multiplication of the expression cassettes or vectors according to the invention, for example in $E.\ coli$. Examples which may be mentioned are ORI (origin of DNA replication), the pBR322 on or the P15A on (Sambrook et al.: Molecular Cloning. A Laboratory Manual, $2^{nd}$ ed. Cold Spring Harbor Laboratory Press, Cold Spring Harbor, N.Y., 1989).

To select cells which have successfully undergone homologous recombination, or else transformation, it will, as a rule, be required additionally to introduce a selectable marker which confers a resistance to a biocide or to an antibiotic to the cells which have successfully undergone recombination. The selection marker permits the selection of the transformed cells from untransformed cells (McCormick et al. (1986) Plant Cell Reports 5:81-84).

The gene constructs can advantageously be introduced into an organism using vectors which comprise the gene construct. Therefore, a further subject matter of the invention relates to said transgenic vectors which comprise a transgenic gene construct for a homofarnesol-ambroxan cyclase.

Vectors may be plasmids, cosmids, phages, viruses, for example. The gene construct can be introduced into the vector (preferably a plasmid vector) via a suitable restriction cleavage site. The resulting vector is first introduced into $E.\ coli$. Correctly transformed $E.\ coli$ are selected, cultured, and the recombinant vector is obtained by methods known to a person skilled in the art. Restriction analysis and sequencing may be used for verifying the cloning step. Preferred vectors are those which make possible the stable integration of the expression cassette into the host genome.

A suitable transgenic organism is generated for example by means of transformation or transfection by means of the corresponding proteins or nucleic acids. The generation of a transformed organism (or of a transformed cell) requires the DNA in question (for example the expression vector), the RNA in question or the protein in question to be introduced into the host cell in question. A multiplicity of methods are available for this process, which is referred to as transformation (or transduction or transfection) (Keown et al. (1990) Methods in Enzymology 185:527-537). Thus, the DNA or RNA can be introduced for example directly by means of microinjection or by bombarding with DNA-coated microparticles. Also, the cell can be permeabilized chemically, for example using polyethylene glycol, so that the DNA can enter the cell via diffusion. The DNA can also be carried out by protoplast fusion with other DNA-comprising units such as minicells, cells, lysosomes or liposomes. Electroporation, where the cells are reversibly permeabilized by an electrical pulse, is another suitable method for introducing DNA.

Stably transformed cells, i.e. those in which the DNA introduced is present in integrated form in the DNA of the host cell, can be selected from untransformed cells when a selectable marker is a component of the DNA introduced. An example of a marker can be for example any gene which is capable of conferring a resistance to antibiotics (such as kanamycin, G 418, bleomycin, hygromycin and the like) (see above). Transformed cells which express such a marker gene are capable of surviving in the presence of concentrations of an antibiotic in question which destroy an untransformed wild type. 89:525-533 used.

"Transgenic" or "recombinant" means in respect of, for example, a nucleic acid sequence, a gene construct or a vector comprising said nucleic acid sequence or an organism transformed with said nucleic acid sequence, gene construct or vector, all those constructs which have originated by recombinant methods and in which either
a) the nucleic acid sequence coding for a homofarnesol-ambroxan cyclase, or
b) a genetic control sequence which is functionally linked to said nucleic acid sequence of a), for example a functional promoter, or
c) (a) and (b)
are not located in their natural genetic environment or have been modified by recombinant methods, it being possible for the modification to be, for example, a substitutions, additions, deletions, inversion or insertions of one or more nucleotide residues. Natural genetic environment means the natural chromosomal locus in the original organism, or the presence in a genomic library. In the case of a genomic library, the natural genetic environment of the nucleic acid sequence is preferably at least partially retained.

Transgenic organisms which are preferred as host or starting organisms are predominantly microorganisms as defined hereinabove. Included within the scope of the invention are, in particular, microorganisms, preferably those transgenic or recombinant cells, which are selected among bacteria, cyanobacteria, fungi and yeast. Preferably, the cell is selected among bacteria from the genera *Escherichia, Corynebacterium, Ralstonia, Clostridium, Pseudomonas, Bacillus, Zymomonas, Rhodobacter, Streptomyces, Burkholderia, Lactobacillus* and *Lactococcus*. Especially preferably, the cell is selected among bacteria of the species *Escherichia coli, Pseudomonas putida, Burkholderia glumae, Streptomyces lividans, Streptomyces coelicolor* and *Zymomonas mobilis*.

As donor organism, i.e. organism from which a homofarnesol-ambroxan cyclase is isolated, there are *Methylococcus capsalatus, Rhodopseudomonas palustris, Bradyrhizobium japonicum, Frankia* spec., *Streptomyces coelicolor, Rhodopseudomonas palustris, Rhodopseudomonas palent, Frankia alni, Bacillus anthracis, Burkholderia ambifaria*, in particular *Zymomonas mobilis* and *Bradyrhizobium japonicum*.

In one variant of the invention, the transgenic organisms, in particular *Streptomyces coelicolor* or *Zymomonas mobilis*, which have endogenous homofarnesol-ambroxan cyclases, demonstrate overexpression of the homofarnesol-ambroxan cyclases.

Overexpression means any form of expression of the homofarnesol-ambroxan cyclases which can be found in addition to the original expression of the wild type.

In one embodiment, the invention relates to the preparation of transgenic *E. coli* which express the gene coding for the homofarnesol-ambroxan cyclases, preferably SEQ ID NO 1. To this end, the gene of the cyclase is amplified, preferably from *Zymomonas mobilis* (SEQ ID NO 1), using primers, for example Zm-SHC_fw and Zm-SHC_rev (SEQ ID NO 3 or 3). The primers are mixed with each other in equimolar amounts. The PCR with genomic DNA of a donor organism, preferably from *Z. mobilis* (LU8910=ATCC31821), is carried out following the manufacturer's instructions using Pwo polymerase (Roche Applied Science) and the following temperature gradient program: 3 min at 95° C.; 30 cycles of 30 sec at 95° C., 30 sec at 50° C., and 3 min at 72° C.; 10 min at 72° C.; 4° C. until use. The PCR product is isolated by agarose gel electrophoresis (1.2% E-gel, invitrogen) and column chromatography (GFX Kit, Amersham Pharmacia) and subsequently sequenced (sequencing primers: Zm-SHC_fw and Zm-SHC_rev). The PCR product was digested with the restriction endonucleases, preferably NdeI and BamHI, and ligated into a suitably cleaved vector, preferably pDHE1650-Vekto [WO 200132890 A1]. The plasmid thus obtained is transformed into *E. coli*, preferably into the strain *E. coli* TG10 pAgro4 [Takeshita S. et al.; Gene (1987), 61: 63] pHSG575.

Inoculated from a suitable preculture, the *E. coli* are cultured, preferably in LBAmp/Spec/Cm (100 µg/l ampicillin; 100 µg/l spectinomycin; 20 µg/l chloramphenicol), 0.1 mM IPTG, 0.5 g/l Rhamnose for 16 h at 37° C., subsequently centrifuged at 5000*g/10 min and optionally stored at 4° C.

In a further embodiment of the invention, the cyclase is isolated from the donor organism or from the transgenic host organism and optionally purified.

The cells are used to prepare a protein extract by suspending the cell pellet in breaking buffer (0.2M Tris/HCl, 0.5M EDTA, pH 8.0), 375 U Benzonase (for example Novagen, 25 U/µl), 40 µl PMSF (100 mM, dissolved in i-PropOH), 5.3 g/100 ml of sucrose and approximately 3.3 mg/100 ml lysozyme. The reaction is mixed and incubated on ice for 30 minutes. Thereafter, the mixture will optionally be frozen at −20° C. After the reaction mixture has been defrosted, it is made up with distilled water and reincubated on ice for 30 minutes. Thereafter, the cells are sonicated 3 times for 3 minutes.

After the disruption, the cell debris was centrifuged off during 60 min at 4° C. and 26 900*g. The supernatant is discarded, and the pellet is resuspended in solubilisation buffer (50 mM Tris/HCl, 10 mM $MgCl_2 \times 6H_2O$, 1% Triton X-100, pH 8.0) and homogenized for approximately 5 min, for example using a Potter. Thereafter, the suspension is kept on ice for 30 min. The homogenized extract is recentrifuged for 1 h at 4° C. and 26 900*g, and the pellet is discarded. The extract can be employed for enzyme assays and can be stored for several weeks at −20° C. without activity loss. The protein content is in the order of 1 mg/ml. The cyclases employed in accordance with the invention can be used as free or as immobilized enzyme in the process according to the invention.

The cyclases used according to the invention can be employed in free or in immobilized form. An immobilized enzyme is understood as meaning an enzyme which is fixed to an inert carrier. Suitable carrier materials, and the enzyme immobilized thereon, are known from EP-A-1149849, EP-A-1 069 183 and from DE-OS 100193773, and from the references cited therein. The disclosure of these publications in this regard is incorporated in its entirety herein by reference. The suitable carrier materials include, for example, clays, clay minerals such as kaolinite, diatomatious earth, perlite, silica, alumina, sodium carbonate, calcium carbonate, cellulose powder, anion exchanger materials, synthetic polymers such as polystyrene, acrylic resins, phenol/formaldehyde resins, polyurethanes and polyolefins, such as polyethylene and polypropylene. To prepare the supported enzymes, the carrier materials are usually employed in a finely particulate form, with porous forms being preferred. The particle size of the carrier material is usually no more than 5 mm, in particular no more than 2 mm (grading curve). It is possible analogously when using the cyclase to choose a free or an immobilized form as a whole-cell catalyst. Examples of carrier materials are Ca alginate and carrageenan. Both enzymes and cells can also be crosslinked directly with glutaraldehyde (crosslinking to give CLEAs). Corresponding and further immobilization methods are described, for example, in J. Lalonde and A. Margolin "Immobilization of Enzymes" in K. Drauz and H. Waldmann, Enzyme Catalysis in Organic Synthesis 2002, Vol. III, 991-1032, Wiley-VCH, Weinheim.

Furthermore, it is possible to use intact cells, optionally quiescent or disrupted cells, cell lysate or cell homogenate.

It is possible to use for the method of the invention growing cells which comprise nucleic acid, nucleic acid constructs or vectors coding for the cyclase. It is also possible to use quiescent or disrupted cells. Disrupted cells mean, for example, cells which have been made permeable by a treatment with, for example, solvents, or cells which have been disrupted via an enzyme treatment, a mechanical treatment (e.g. French press or ultrasound) or by any other method. The crude extracts obtained in this way are advantageously suitable for the method of the invention. It is also possible to use purified or partially purified enzymes for the method. Immobilized microorganisms or enzymes are also suitable and can advantageously be used in the reaction.

The process of the invention can be carried out batchwise, semi-batchwise or continuously.

The reaction can be carried out as a batch process or else as a fed-batch process.

The product is subsequently purified by extraction and/or distillation.

Another subject of the present invention is the use of a polypeptide with the activity of a homofarnesol-ambroxan cyclase for the biocatalytic reaction of homofarnesol to give ambroxan.

Yet another subject of the present invention is the use of a polypeptide with the activity of a homofarnesol-ambroxan cyclase for the biocatalytic reaction of homofarnesol to give ambroxan, wherein the polypeptide is encoded by a nucleic acid molecule comprising at least one nucleic acid molecule selected from the group consisting of:
 a) nucleic acid molecule which codes for a polypeptide comprising the in SEQ ID NO 2, 5, 6, 7, 8, 9, 10 or 11;
 b) nucleic acid molecule which comprises at least one polynucleotide of the sequence shown in SEQ ID NO 1;
 c) nucleic acid molecule which codes for a polypeptide whose sequence has an identity of at least 46% to the sequences SEQ ID NO 2, 5, 6, 7, 8, 9, 10 or 11;
 d) nucleic acid molecule according to (a) to (c), which for a functionally equivalent polypeptide or a fragment of the sequence according to SEQ ID NO 2, 5, 6, 7, 8, 9, 10 or 11;
 e) nucleic acid molecule, coding for a functionally equivalent polypeptide with the activity of a homofarnesol-ambroxan cyclase, which is obtained by amplifying a nucleic acid molecule from a cDNA library or from a genomic library using the primers according to sequence nos. 3 and 4, or by chemically synthesizing the respective gene;
 f) nucleic acid molecule, coding for a functionally equivalent polypeptide with the activity of a homofarnesol-ambroxan cyclase which hybridizes with a nucleic acid molecule according to (a) to (c) under stringent conditions;
 g) nucleic acid molecule, coding for a functionally equivalent polypeptide with the activity of a homofarnesol-ambroxan cyclase, which can be isolated from a DNA library using a nucleic acid molecule according to (a) to (c) or their partial fragments of at least 15 nt, preferably 20 nt, 30 nt, 50 nt, 100 nt, 200 nt or 500 nt by way of probe under stringent hybridization conditions; and
 h) nucleic acid molecule, coding for a functionally equivalent polypeptide with the activity of a homofarnesol-ambroxan cyclase, where the sequence of the polypeptide has an identity of at least 46% to the sequences SEQ ID NO 2, 5, 6, 7, 8, 9, 10 or 11;
 i) nucleic acid molecule, coding for a functionally equivalent polypeptide with the activity of a homofarnesol-ambroxan cyclase, where the polypeptide is encoded by a nucleic acid molecule selected from the group of those described in a) to h) and has been isolated, or can be isolated, by means of a monoclonal antibody,
 j) nucleic acid molecule, coding for a functionally equivalent polypeptide with the activity of a homofarnesol-ambroxan cyclase, where the polypeptide has an analogous or similar binding site as a polypeptide encoded by a nucleic acid molecule selected from the group of those described in a) to h).

The examples which follow are intended to illustrate the invention, but without imposing any limitation. Reference is made to the enclosed figures, in which:

Experimental Part

EXAMPLES

Example 1

Cloning of Zm-SHC and Expression in *E. coli*

Using the oligonucleotides Zm-SHC_fw and Zm-SHC_rev, it is possible to amplify the cyclase gene from *Zymomonas mobilis*.

Primers:

| Primer No. | Sequence (5'->3') | Position |
|---|---|---|
| Zm-SHC_fw | gcgctgttt<u>catatg</u>ggtattgaca (SEQ ID NO: 3) | N-terminal primer |
| Zm-SHC_rev | gcgcttaccct<u>ggatcc</u>tcgaaaat (SEQ ID NO: 4) | C-terminal primer |

100 ng of each of the primers Zm-SHC_fw and Zm-SHC_rev were mixed in equimolar amounts. The PCR with genomic DNA from *Z. mobilis* (ATCC31821) was carried out as specified by the manufacturer using Pwo polymerase (Roche Applied Science) and the following temperature gradient program: 3 min at 95° C., 30 cycles of 30 sec at 95° C., 30 sec at 50° C., and 3 min at 72° C.; 10 min at 72° C.; 4° C. until use. The PCR product (~2.2 kb) was isolated by agarose gel electrophoresis (1.2% E-gel, Invitrogen) and column chromatography (GFX kit, Amersham Pharmacia) and subsequently sequenced (sequencing primers: Zm-SHC_fw and Zm-SHC_rev). The sequence obtained corresponds to the published sequence.

The PCR product was digested with the restriction endonucleases NdeI and BamHI and ligated into the correspondingly digested vector pDHE19.2. Sequencing the resulting plasmids gave the nucleic acid sequence shown in Seq-ID1.

The plasmid pDHE-Zm-SHC-1 was transformed into the strain *E. coli* TG10 pAgro4 pHSG575 [Takeshita et al., Gene 1987, 61:63-74; Tomoyasu et al., Mol Microbiol 2001, 40:397-413]. The recombinant *E. coli* were named *E. coli* LU15568.

Example 2a

Providing Recombinant Homofarnesol Cyclase from *Z. mobilis* (SEQ ID NO 2)

Inoculated from a corresponding 2 ml preculture, *E. coli* LU15568 was grown in 20 ml LB-Amp/Spec/Cm (100 µg/l ampicillin; 100 µg/l spectinomycin; 20 µg/l chloramphenicol), 0.1 mM IPTG, 0.5 g/l rhamnose in 100 ml Erlenmeyer flasks (with baffles) for 16 h at 37° C., centrifuged at 5000*g/ 10 min and stored at 4° C. Protein extract was prepared by suspending the cell pellet in 15 ml breaking buffer (0.2M Tris/HCl, 0.5M EDTA, pH 8.0), 375 U benzonase (e.g. Novagen, 25 U/µL), 40 µL PMSF (100 mM, dissolved in i-PropOH), 0.8 g sucrose and approx. 0.5 mg of lysozyme. The batch was mixed and incubated for 30 min on ice. Thereafter, the mixture was frozen at −20° C.

After defrosting, the mixture was made up to approximately 40 ml with distilled water and reincubated on ice for 30 min.

Thereafter, the cells were sonicated three times for 3 min (HTU-Soni 130, G. Heinemann, Schwäbisch-Hall, amplitude 80%, 15" pulse/15" pause).

After the disruption, the cell debris was centrifuged off during 60 min at 4° C. and 26 900*g. The supernatant was discarded and the pellet was resuspended in 100 ml of solubilization buffer (50 mM Tris/HCl, 10 mM $MgCl_2 \times 6H_2O$, 1% Triton X-100, pH 8.0) and comminuted in a Potter for approximately 5 min. Thereafter, the suspension was held on ice for 30 min.

The homogenized extract was recentrifuged for 1 h at 4° C. and 26 900*g, and the pellet was discarded. The extract was employed for the enzyme assays and can be stored for several weeks at −20° C. without activity losses. The protein content is in the order of 1 mg/ml.

Example 2b

Providing Recombinant Homofarnesol-Cyclase from *Bradyrhizobium japonicum* (SEQ ID NO 5)

Homofarnesol-cyclase from *Bradyrhizobium japonicum* was prepared as in example 2a.

Example 3a

Determination of the Activity of the Recombinant Homofarnesol Cyclase (SEQ ID NO 2) from *E. coli* LU15568

Homofarnesol (1,(3Z,7E-4,8,12-trimethyltrideca-3,7,11-trien-1-ol) was incubated with the protein preparation described in example 2a. Specifically, 4 ml of protein preparation, 0.5 ml of Na citrate buffer (1M sodium citrate pH 4.9), 0.5 ml of homofarnesol solution (100 mM in 0.1M Na citrate buffer, pH 6.5 with 2% (w/w) taurodeoxycholate) were mixed with each other and incubated with stirring at 30° C. A control reaction with the same composition was incubated at 60° C., however.

After incubation for 16 hours, the mixtures were extracted using 10 ml of hexane/n-propanol 3:2, and the organic phase was evaporated to dryness.

The residue was taken up in 200 µl of dichloromethane and employed for the GC or GC/MS analysis.

Using the analyses shown in example 4, a conversion rate of 41% (>>20.5 µmol 2) was determined.

By way of comparison, reactions of homofarnesol with the known squalene-hopene cyclase from *Alicyclobacillus acidocaldarius* achieved a conversion rate of 1.2%.

Example 3b

Determination of the Activity of the Recombinant Homofarnesol Cyclase (SEQ ID NO 5) from *E. coli*

The enzymatic activity of the biocatalyst from *Bradyrhizobium japonicum* which had been produced recombinantly in *E. coli* corresponds to that of Zm-SHC. After incubation of a 20 mM homofarnesol solution with cell homogenate (amount of protein: 31 mg) at 37° C. for 3 hours, 26.4% of the homofarnesol were reacted to give ambroxan. Under identical conditions, recombinant Zm-SHC gave a conversion rate of 22.4%.

Example 4

Analyses

Reaction/Quantification

The reaction of homofarnesol (1) to ambroxan (2) can be determined using the following GC system:
Column: 10 m Optima 1
Temperature Profile:
0': 100° C.
  15° C./min
14.7': 320° C.
34.7' 320° C.
Injector temperature: 320° C.
RT: homofarnesol approx. 12.5'; ambroxan: approx. 11.4'

A calibration series, which was used to determine the concentration of unknown samples, was prepared using authentic material.
Identification The identification was performed by means of capillary GC/MS of the positive ions following electron impact ionization (EI) and chemical ionization (CI) with ammonia. Equipment: GC (HP 6890) coupled with two MSDs (HP 5973) for EI and CI ionization.

| GC CONDITIONS: | |
|---|---|
| Separation column: | DB-1 |
| Length: | 30 m |
| Internal diameter: | 250 µm |
| Film thickness: | 0.25 µm |
| Carrier gas: | He |
| Flow rate: | 1.2 ml/min |
| Split ratio: | 1:60 |
| Oven temperature: | 100° C., 5K/min to 200° C., 5 min isothermic, 30K/min to 300° C., 50 min isothermic |
| Injector temperature: | 250° C. |
| Transfer line temperature: | 300° C. |
| Injection quantity: | 0.2 µl |
| Sample preparation: | Direct injection |

| MS CONDITIONS | | | |
|---|---|---|---|
| EI: | | CI: | |
| Scanning range: | 25-750 amu | Scanning range: | 75-800 amu |
| Ionization energy: | 70 eV | | |

We claim:

1. A process for the production of ambroxan derivatives of formula (2), comprising biocatalytically converting homofarnesol derivatives of formula (1) to ambroxan derivatives of formula (2) using a polypeptide with the activity of a homofarnesol-ambroxan cyclase,

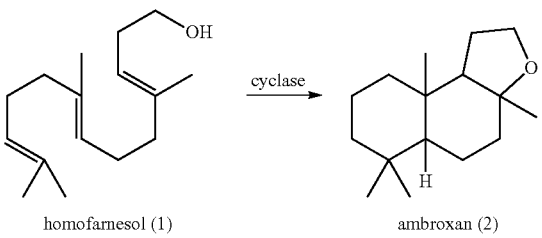 [SMILES: CC(C)=CCC/C(C)=C/CC/C(C)=C/CCO ; CC1(C)CCCC2(C)C1CCC1(C)OCCC12]

homofarnesol (1)    ambroxan (2)

wherein the polypeptide is encoded by a nucleic acid molecule selected from the group consisting of:
   a) a nucleic acid molecule which encodes a polypeptide comprising the amino acid sequence of SEQ ID NO: 2 or SEQ ID NO: 5;
   b) a nucleic acid molecule which comprises the polynucleotide sequence of SEQ ID NO: 1; and
   c) a nucleic acid molecule which encodes a polypeptide having at least 95% sequence identity to the amino acid sequence of SEQ ID NO: 2 or SEQ ID NO: 5, wherein said polypeptide has the activity of a homofarnesol-ambroxan cyclase.

2. The process of claim 1, wherein the polypeptide is present in a form selected from the group consisting of:
   a) a free, optionally purified or partially purified polypeptide with the activity of a homofarnesol-ambroxan cyclase;
   b) an immobilized polypeptide with the activity of a homofarnesol-ambroxan cyclase;
   c) the polypeptide of a) or b), isolated from a cell;
   d) an intact cell, optionally a quiescent or disrupted cell, comprising said polypeptide with the activity of a homofarnesol-ambroxan cyclase;
   e) a cell lysate or cell homogenate of the cell of d).

3. The process of claim 2, wherein the cells is a transgenic microorganism expressing at least one heterologous nucleic acid molecule encoding said polypeptide with the activity of a homofarnesol-ambroxan cyclase.

4. The process of claim 1, wherein the starting material employed for the production of ambroxan is citral, which is reacted in a plurality of steps to give homofarnesol.

5. The process of claim 1, wherein ambroxan is produced in single-phase aqueous systems or in two-phase systems.

6. The process of claim 1, wherein ambroxan is produced batchwise, fed-batch-wise or continuously.

7. The process of claim 1, wherein the conversion of homofarnesol to ambroxan takes place at a temperature in the range of from 0 to 45° C. (60° C.) and/or at a pH in the range of from 4 to 8.

8. The process of claim 1, wherein the polypeptide with the activity of a homofarnesol-ambroxan cyclase is from a microorganism which overexpresses a homofarnesol-ambroxan cyclase, wherein said microorganism is selected from the group consisting of the bacteria of the genus *Escherichia*, *Corynebacterium*, *Ralstonia*, *Clostridium*, *Pseudomonas*, *Bacillus*, *Zymomonas*, *Rhodobacter*, *Streptomyces*, *Burkholderia*, *Lactobacillus* and *Lactococcus*.

9. The process of claim 1, wherein the polypeptide with the activity of a homofarnesol-ambroxan cyclase is isolated from a microorganism selected from the group consisting of *Methylococcus capsalatus*, *Rhodopseudomonas palustris*, *Frankia* spec., *Streptomyces coelicolor*, *Rhodopseudomonas palent*, *Frankia alni*, *Bacillus anthracis*, *Burkholderia ambifaria*, *Zymomonas mobilis* and *Bradyrhizobium japonicum*.

10. The process of claim 1, wherein the polypeptide with the activity of a homofarnesol-ambroxan cyclase is isolated from a transgenic bacterium of the species *Escherichia coli*, *Pseudomonas putida*, *Burkholderia glumae*, *Streptomyces lividans*, *Streptomyces coelicolor*, *Methylococcus capsalatus*, *Rhodopseudomonas palustris*, *Frankia* spec., *Rhodopseudomonas palent*, *Frankia alni*, *Bacillus anthracis*, *Burkholderia ambifaria*, *Zymomonas mobilis* or *Bradyrhizobium japonicum*, and wherein said transgenic bacterium overexpress a homofarnesol-ambroxan cyclase.

11. The process of claim 1, wherein the main activity of said polypeptide with the activity of a homofarnesol-ambroxan cycase is reaction with homofarnesol.

12. The process of claim 1, wherein ambroxan is produced.

13. The process of claim 12, further comprising purifying ambroxan.

14. The process of claim 1, wherein the conversion of homofarnesol to ambroxan takes place at a temperature of 25, 30, 40, 50 or 60° C.

15. A vector comprising a nucleic acid molecule encoding a polypeptide with the activity of a homofarnesol-ambroxan cyclase, wherein said nucleic acid molecule is selected from the group consisting of:
- a) a nucleic acid molecule encoding a polypeptide comprising the amino acid sequence of SEQ ID NO: 2 or SEQ ID NO: 5;
- b) a nucleic acid molecule comprising the polynucleotide sequence of SEQ ID NO: 1; and
- c) a nucleic acid molecule encoding a polypeptide having at least 95% sequence identity to the amino acid sequence of SEQ ID NO: 2 or SEQ ID NO: 5, wherein said polypeptide has the activity of a homofarnesol-ambroxan cyclase.

16. A microorganism comprising the vector of claim 15.

* * * * *